(12) United States Patent
Bekele et al.

(10) Patent No.: US 8,722,164 B2
(45) Date of Patent: May 13, 2014

(54) POLYMERIC FILM FOR USE IN BIOPROCESSING APPLICATIONS

(71) Applicant: Cryovac, Inc., Duncan, SC (US)

(72) Inventors: Solomon Bekele, Taylors, SC (US); Patrick Wayne Thompson, Greenville, SC (US)

(73) Assignee: Cryovac, Inc., Duncan, SC (US)

( * ) Notice: Subject to any disclaimer, the term of this patent is extended or adjusted under 35 U.S.C. 154(b) by 0 days.

(21) Appl. No.: 13/874,536

(22) Filed: May 1, 2013

(65) Prior Publication Data

US 2013/0302894 A1 Nov. 14, 2013

Related U.S. Application Data

(60) Provisional application No. 61/645,698, filed on May 11, 2012.

(51) Int. Cl.
| | | |
|---|---|---|
| *C12N 5/00* | (2006.01) | |
| *C12N 5/02* | (2006.01) | |
| *B29D 22/00* | (2006.01) | |
| *B29D 23/00* | (2006.01) | |
| *B32B 1/08* | (2006.01) | |
| *B32B 27/08* | (2006.01) | |
| *C08L 23/04* | (2006.01) | |
| *C08L 77/00* | (2006.01) | |
| *C12M 1/00* | (2006.01) | |

(52) U.S. Cl.
CPC .................. *C12M 23/26* (2013.01); *C12N 5/00* (2013.01); *B29D 22/00* (2013.01); *B29D 23/00* (2013.01); *B32B 1/08* (2013.01); *B32B 27/08* (2013.01); *C08L 23/04* (2013.01); *C08L 2207/06* (2013.01); *C08L 77/00* (2013.01)

USPC ....... 428/36.7; 428/212; 428/483; 428/476.9; 428/475.2; 428/474.7; 428/35.7; 428/36.6

(58) Field of Classification Search
CPC ........... C12M 23/26; C12N 5/00; C12N 5/02; B29D 22/00; B29D 23/00; B32B 1/08; B32B 27/08; C08L 23/04; C08L 2207/06; C08L 77/00
USPC ............ 435/394; 428/212, 483, 476.9, 475.2, 428/474.7, 35.7, 36.6, 36.7
See application file for complete search history.

(56) References Cited

U.S. PATENT DOCUMENTS

| | | |
|---|---|---|
| 3,741,253 A | 6/1973 | Brax et al. |
| 4,278,738 A | 7/1981 | Brax et al. |

(Continued)

OTHER PUBLICATIONS

Sandstrom, Disposable vs. Traditional Equipment—A Facility-Wide View, www.aiche.org/cep, Jul. 2009, pp. 30-35.

(Continued)

*Primary Examiner* — Michael C Miggins
(74) *Attorney, Agent, or Firm* — Ashley D. Wilson

(57) ABSTRACT

The presently disclosed subject matter is directed to a polymeric films suitable for use in a wide variety of applications, including (but not limited to) the formation of bioprocessing containers. Particularly, the disclosed films comprise a first barrier layer comprising polyglycolic acid, polyamide, EVOH, and/or an EVOH blend and a second barrier layer comprising EVOH. The dual barrier layers of the film maintain a high gas barrier under a variety of relative humidity conditions. In addition, the disclosed film is biologically inert and free from film surface-modifying additives such that the film does not inhibit the growth of biological cell cultures.

20 Claims, 5 Drawing Sheets

(56) References Cited

U.S. PATENT DOCUMENTS

| | | |
|---|---|---|
| 4,284,458 A | 8/1981 | Schirmer |
| 4,551,380 A | 11/1985 | Schoenberg |
| 5,853,639 A | 12/1998 | Kawakami et al. |
| 5,988,422 A | 11/1999 | Vallot |
| 6,046,251 A | 4/2000 | Kawakami et al. |
| 6,769,227 B2 | 8/2004 | Mumpower et al. |
| 7,179,868 B2 | 2/2007 | Yamane et al. |
| 7,776,415 B2 | 8/2010 | Inaba et al. |
| 7,785,682 B2 | 8/2010 | Sato et al. |
| 7,812,181 B2 | 10/2010 | Ogawa et al. |
| 7,976,919 B2 | 7/2011 | Sato et al. |
| 2010/0215858 A1 | 8/2010 | Yamane et al. |
| 2011/0027428 A1 | 2/2011 | Bekele |
| 2011/0027590 A1 | 2/2011 | Abe |
| 2011/0108185 A1 | 5/2011 | Hokari et al. |
| 2011/0229722 A1 | 9/2011 | Rivett et al. |
| 2012/0107542 A1* | 5/2012 | Nelson et al. ............ 428/36.92 |
| 2012/0208039 A1 | 8/2012 | Barbaroux et al. |
| 2013/0078174 A1 | 3/2013 | Takayasu et al. |

OTHER PUBLICATIONS

Steiger et al., Interlaboratory Test for Detection of Cytotoxic Leachables Arising From Single-Use Bags, Chemie Ingenieur Technik 2013, 85, No. I-2, 26-28.

* cited by examiner

US 8,722,164 B2

POLYMERIC FILM FOR USE IN BIOPROCESSING APPLICATIONS

CROSS REFERENCE TO RELATED APPLICATIONS

This application claims priority to U.S. Provisional Patent Application No. 61/645,698, filed May 11, 2012, the entirety of which is incorporated by reference herein.

FIELD OF THE INVENTION

The presently disclosed subject matter generally relates to polymeric films suitable for use in constructing disposable containers for bioprocessing applications. More particularly, the presently disclosed films maintain an exemplary gas barrier under low, intermediate, and high relative humidity conditions and do not inhibit the growth of biological cell cultures, cellular aggregates, particles, tissues, and the like.

BACKGROUND

The development and commercialization of many processes in the fields of medicine, chemistry, and agriculture require the use of bioprocessing containers. Cells have typically been grown in vitro in glass, metal, or hard plastic vessels. However, because these culture vessels are not disposable, they are expensive and require maintenance. Particularly, to maintain a sterile or aseptic environment for cell culture, the vessels require sterilization, usually by autoclave or aseptic disinfection. Thus, they must be washed and sterilized prior to and/or subsequent to use. In addition, because glass, metal, and hard plastic vessels are not disposable, it is necessary to have a large amount of space to accommodate storage.

In addition, the expense of producing cells, biopharmaceuticals, biologicals, and the like is often exacerbated by the required cleaning, sterilization, and validation of conventional bioprocessing containers (i.e., metal, glass, or hard plastic vessels). Attempts have been made to solve this problem with the development of pre-sterilized disposable bioprocessing containers constructed from sheets of flexible, gas-impermeable film that conventionally include at least one ethylene vinyl alcohol (EVOH) layer to increase the gas barrier properties of the structure. As is well known, the barrier properties of EVOH are suitable in low humidity conditions, but degrade substantially when exposed to high humidity. In addition, films typically used for flexible cell culture bags include film surface modifying additives (such as antifogging agents, antistatic agents, anti-blocking agents, and the like) that inhibit cell culture growth.

Therefore, it would be beneficial to provide a flexible film suitable for bioprocessing applications that maintains barrier properties at low, intermediate, and high humidity conditions. It would also be advantageous if the disclosed flexible film was free of surface-modifying additives such that the growth of biological cell cultures is supported.

SUMMARY

In some embodiments, the presently disclosed subject matter is directed to a multilayer film comprising a sealant layer comprising about 5-95 weight percent olefin hydrocarbon polymer with $T_g \geq 25°$ C. and about 95-5 weight percent alpha-olefin copolymer. The disclosed film also comprises a first barrier layer comprising polyglycolic acid, polyamide, EVOH, an EVOH blend, or combinations thereof, wherein the first barrier layer is positioned adjacent to the sealant layer. The film further comprises a skin layer comprising PET or a PET blend (wherein at least one PET in the blend is amorphous and has $T_g \geq 50°$ C.), or polyamide, or a polyamide blend (wherein at least one polyamide in the blend is amorphous and has $T_g \geq 50°$ C.). The film further comprises a second barrier layer comprising EVOH, wherein the second barrier layer is positioned adjacent to the skin layer. The disclosed film has an oxygen transmission rate of less than about 500 cc/m$^2$-day-atm at 73° F. at high, intermediate, and low relative humidity conditions, in accordance with ASTM D-3985.

In some embodiments, the presently disclosed subject matter is directed to a bioprocessing container comprising at least first and second films constructed from the disclosed film, wherein the sidewalls of the container are sealed along their edges to define an interior compartment for housing a product. For example, the presently disclosed subject matter can include embodiments wherein 4 film webs are joined together to form a double walled container.

In some embodiments, the presently disclosed subject matter is directed to a method of culturing cells. The disclosed method comprises providing the disclosed bioprocessing container, introducing a liquid medium into the interior compartment of the container, inoculating the liquid medium with cells, and incubating the cells within the interior container under suitable conditions for cell growth.

DETAILED DESCRIPTION

I. General Considerations

Figure 1:
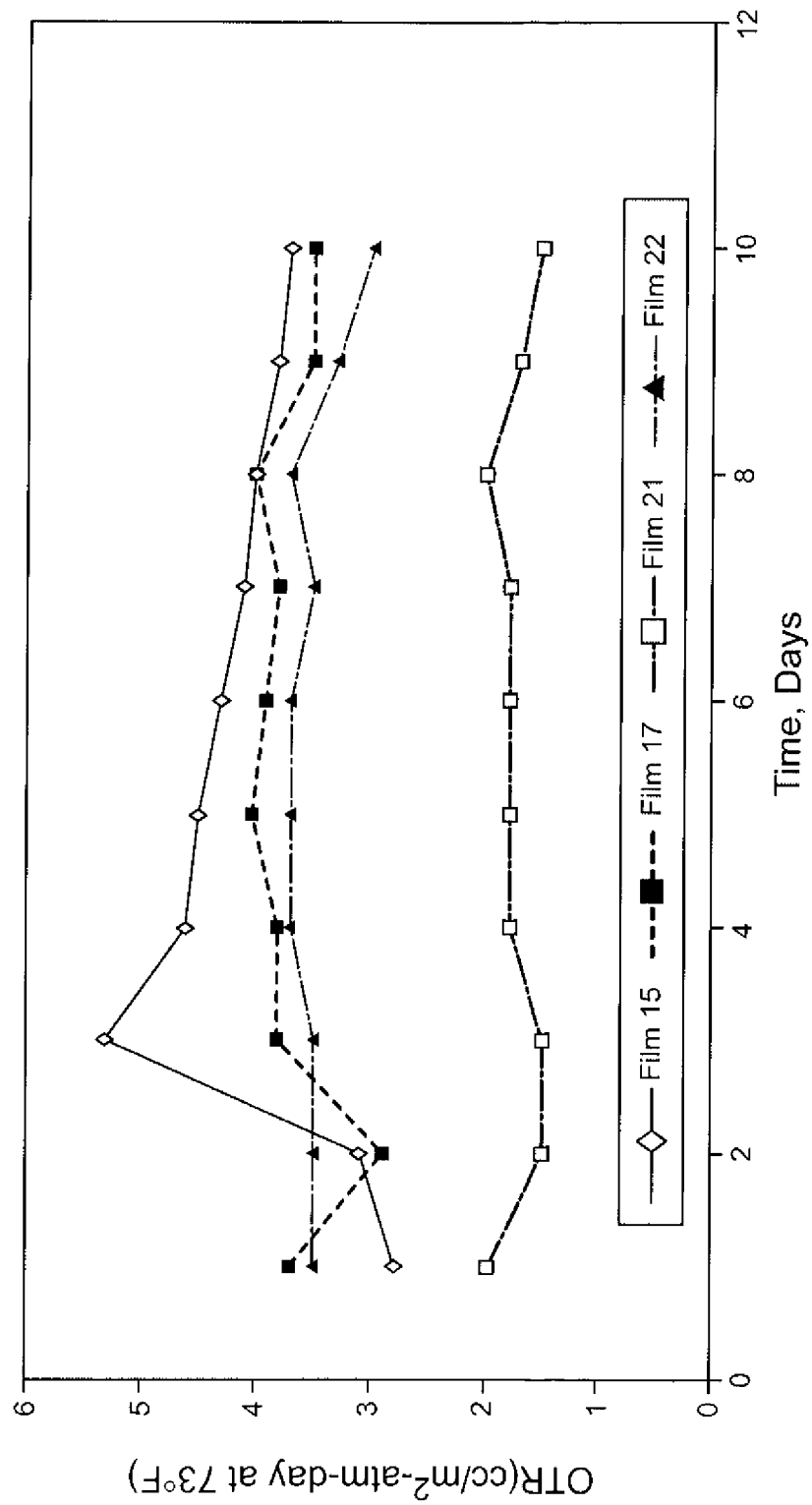
FIG. 1 is line graph illustrating the oxygen transmission rate of disclosed Films 15, 17, 21, and 22 at 100/50% (in/out) relative humidity and 73° F. over a 10 day time course.

The presently disclosed subject matter is directed to a polymeric film suitable for use in a wide variety of applications, such as (but not limited to) the formation of bioprocessing containers. Particularly, the disclosed film comprises two barrier layers (a first barrier layer comprising polyglycolic acid, polyamide, EVOH, and/or an EVOH blend and a second barrier layer comprising EVOH) to maintain a high gas barrier under low, intermediate, and high relative humidity conditions. In addition, the disclosed film is biologically inert and free from film surface-modifying additives such that the growth of biological cell cultures is not inhibited.

II. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs.

Following long standing patent law convention, the terms "a", "an", and "the" refer to "one or more" when used in the subject application, including the claims. Thus, for example, reference to "a film" includes a plurality of such films, and so forth.

Unless indicated otherwise, all numbers expressing quantities of components, reaction conditions, and so forth used in the specification and claims are to be understood as being modified in all instances by the term "about." Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, percentage, and the like can encompass variations of, and in some embodiments, ±20%, in some embodiments ±10%, in some embodiments ±5%, in some embodiments ±1%, in some embodiments ±0.5%, and in some embodiments ±0.1%, from the specified amount, as such variations are appropriated in the disclosed film and methods.

As used herein, the term "adjacent" as applied to film layers refers to the positioning of two layers in contact with one another with or without an intervening layer (such as a tie layer), adhesive, or other layer therebetween.

As used herein, the phrase "alpha olefin copolymer" or "ethylene/alpha olefin copolymer" refers to such heterogeneous materials as linear low density polyethylene (LLDPE) with a density usually in the range of from about 0.915 g/cm$^3$ to about 0.930 g/cm$^3$, linear medium density polyethylene (LMDPE) with a density usually in the range of from about 0.930 g/cm$^3$ to about 0.945 g/cm$^3$, and very low and ultra low density polyethylene (VLDPE and ULDPE) with a density lower than about 0.915 g/cm$^3$. In some embodiments, the term can refer to homogeneous polymers such as metallocene-catalyzed EXACT® and EXCEED® homogeneous resins obtainable from Exxon, single-site AFFINITY® resins obtainable from Dow, and TAFMER® homogeneous ethylene-alpha-olefin copolymer resins obtainable from Mitsui. All these materials can include co-polymers of ethylene with one or more co-monomers selected from (C4-C10)-alpha-olefin such as butene-1, hexene-1, octene-1, etc., in which the molecules of the copolymers include long chains with relatively few side chain branches or cross-linked structures.

As used herein, the terms "barrier" and "barrier layer" as applied to films and/or film layers, refer to the ability of a film or film layer to serve as a barrier to gases and/or odors. Examples of polymeric materials with low oxygen transmission rates useful in such a layer can include: ethylene/vinyl alcohol copolymer (EVOH), polyvinylidene dichloride (PVDC), vinylidene chloride copolymer such as vinylidene chloride/methyl acrylate copolymer, vinylidene chloride/vinyl chloride copolymer, polyamide, co-polyamide, PGA, polyester, polyacrylonitrile (available as Barex™ resin), or blends thereof. Oxygen barrier materials can further comprise high aspect ratio fillers that create a tortuous path for permeation (e.g., nanocomposites). Oxygen barrier properties can be further enhanced by the incorporation of an oxygen scavenger, such as an organic oxygen scavenger. In some embodiments, metal foil, metallized substrates (e.g., metallized polyethylene terephthalate ((PET)), metallized polyamide, and/or metallized polypropylene), and/or coatings comprising SiOx or AlOx compounds can be used to provide low oxygen transmission to a package. In some embodiments, a barrier layer can have a gas (e.g., oxygen) permeability of less than or equal to about 500 cc/m$^2$/24 hrs/atm at 73° F., in some embodiments less than about 100 cc/m$^2$/24 hrs/atm at 73° F., in some embodiments less than about 50 cc/m$^2$/24 hrs/atm at 73° F., and in some embodiments less than about 25 cc/m$^2$/24 hrs/atm at 73° F., in accordance with ASTM D-3985. The entire contents of all referenced ASTMs herein are incorporated by reference.

As used herein, the term "biologically inert" refers to a property of a material whereby the material does not chemically react with biological material and/or does not scalp or leach into media or biological material.

The term "bioprocessing" as used herein refers to any process that uses living cells or their components (e.g., bacteria, enzymes, chloroplasts, and the like). For example, in some embodiments, bioprocessing can include processes for the production of a product by culturing cells or microorganisms, processes of culturing cells or microorganisms, and/or processes for the bioconversion of one material to another.

The term "bioprocessing container" as used herein refers to a container suitable for use in bioprocessing applications (such as, but not limited to, growing cell cultures). Alternatively or in addition, bioprocessing containers can be used to house any of a wide variety of biological fluids such as serum, buffers, and ultrapure water.

The term "bulk layer" as used herein refers to a layer used to increase the abuse-resistance, toughness, modulus, etc., of a film. In some embodiments, the bulk layer can comprise polyolefin (including but not limited to) at least one member selected from the group comprising ethylene/alpha-olefin copolymer, ethylene/alpha-olefin copolymer plastomer, low density polyethylene, and/or linear low density polyethylene and polyethylene vinyl acetate copolymers.

The term "cell" as used herein refers to any cellular matter that can be maintained in a bioprocessing container. For example, in some embodiments, the term "cell" can include (but is not limited to) eukaryotic cells (such as yeast, insect, or mammalian), but in some embodiments can be bacterial. It should be understood that the term "cell" can also encompass any of a wide variety of cellular components.

The term "container" as used herein includes, but is not limited to, any of a wide variety of packages or storage devices including pouches, bags, boxes, cartons, envelopes, bottles, and the like constructed from a polymeric film. The term "container" also includes any packaging or storage device that has been designed for or in support of bioprocessing applications.

The term "directly adjacent" as used herein refers to adjacent layers that are in contact with another layer without any tie layer, adhesive, or other layer therebetween.

As used herein, the term "ethylene vinyl alcohol" or "EVOH" refers to ethylene/vinyl alcohol copolymer. EVOH includes saponified or hydrolyzed ethylene/vinyl acetate copolymers, and refers to a vinyl alcohol copolymer having an ethylene comonomer, prepared by (for example) hydrolysis of vinyl acetate copolymers, or by chemical reactions with polyvinyl alcohol. In some embodiments, the degree of hydrolysis can be at least 50% or at least 85%.

The term "EVOH blend" refers to a blend of two or more EVOH copolymers. Thus, the term "blend" implies the intermixing of two or more units. Similarly, a polyamide blend refers to a blend of two or more polyamides, a PET blend refers to a blend of two or more PETs, and so forth.

As used herein, the term "film" can be used in a generic sense to include plastic web, regardless of whether it is film or sheet.

The term "flexible" is used herein to define specific polymeric materials as well as characteristics of a resulting container whereby improved flexibility and/or collapsibility of the container is obtained by the use of these specific polymeric materials. Flexible materials can in some embodiments be characterized by a modulus of less than about 50,000 PSI and in some embodiments less than 40,000 PSI (ASTM D-872-81).

As used herein, the term "glass transition temperature" or "Tg" refers to the temperature at which, when cooling a polymer from a molten state, the mechanical properties of the polymer change from those of a rubber (elastic) to those of a glass (brittle). Glass transition temperature can be determined in accordance with ISO 3146-C or ASTM D-3418.

As used herein, the term "high relative humidity" refers to a relative humidity of about 70-100%; in some embodiments, about 75-100%; in some embodiments, about 80-100% and in some embodiments, about 85-100%.

The term "homopolymer" refers to a polymer resulting from the polymerization of a single monomer and consisting of a single type of repeating unit.

The term "inoculating" or "inoculation" as used herein refers to the introduction of at least one biological component (such as, for example, a cell) to a medium to begin a culture.

In some embodiments, "intermediate relative humidity" refers to a relative humidity level of about 30-70%; in some embodiments, about 40-60%; and in some embodiments, about 45-55%.

The term "liquid medium" as used herein includes any liquid medium that can be used for conventional methods of bioprocessing, such as (but not limited to) cell culture medium.

As used herein, the term "low relative humidity" refers a relative humidity level of about 0-30%; in some embodiments, about 0-20%; in some embodiments, about 0-10%; and in some embodiments, about 0-5%.

The term "multilayer film" as used herein refers to a thermoplastic material, generally in sheet or web form, having one or more layers formed from polymeric or other materials that are bonded together by any conventional or suitable method, including one or more of the following: coextrusion, extrusion coating, lamination, vapor deposition coating, solvent coating, emulsion coating, and/or suspension coating.

The term "olefin hydrocarbon polymer" or "polymer of an olefin hydrocarbon" as used herein refers polymers prepared by the polymerization of olefin hydrocarbons, particularly styrene, acrylonitrile, vinyl chloride, vinylidene chloride, and the like, as well as the various acrylates, methacrylates, acrylamides, and their derivatives.

The term "oxygen transmission rate" or "OTR" refers to the rate of oxygen gas passing through an entire film structure. OTR is measured according to ASTM D3985, a test known to those of ordinary skill in the art.

As used herein, the term "polyglycolic acid" or "PGA" refers to polymers comprising glycolic acid as a main component and includes copolymerized polyglycolic acids obtained by copolymerization of polyglycolic acids with other ester bond forming components, such as hydroxycarboxylic acid, lactones, dicarboxylic acid, diol, and substances obtained by mixing these polymers with additives as subcomponents.

As used herein, the term "polymer" refers to the product of a polymerization reaction, and can be inclusive of homopolymers, copolymers, terpolymers, etc. In some embodiments, the layers of a film can consist essentially of a single polymer, or can have additional polymer together therewith, i.e., blended therewith.

As used herein, the term "seal" refers to any seal of a first region of an outer film surface to a second region of an outer film surface, including heat or any type of adhesive material, thermal or otherwise. In some embodiments, the seal can be formed by heating the regions to at least their respective seal initiation temperatures. The sealing can be performed by any one or more of a wide variety of methods, including (but not limited to) using a heat seal technique (e.g., melt-bead sealing, thermal sealing, impulse sealing, dielectric sealing, radio frequency sealing, ultrasonic sealing, hot air, hot wire, infrared radiation).

As used herein, the phrases "seal layer", "sealing layer", "heat seal layer", and "sealant layer", refer to an outer film layer, or layers, involved in the sealing of the film to itself, another film layer of the same or another film, and/or another article that is not a film. It should also be recognized that in general, up to the outer 1-10 mils of a film can be involved in the sealing of the film to itself or another layer. In general, a sealant layer sealed by heat-sealing layer comprises any thermoplastic polymer. In some embodiments, the heat-sealing layer can comprise, for example, thermoplastic polyolefin, thermoplastic polyamide, thermoplastic polyester, and thermoplastic polyvinyl chloride. In some embodiments, the heat-sealing layer can comprise thermoplastic polyolefin.

As used herein, the term "skin layer" refers to an outer layer of a multilayer film. Such outer film layers are subject to abuse during storage and handling of the packaged products.

As used herein, the term "tie layer" refers to an internal film layer having the primary purpose of adhering two layers to one another. In some embodiments, tie layers can comprise any nonpolar polymer having a polar group grafted thereon, such that the polymer is capable of covalent bonding to polar polymers such as polyamide, PGA, and/or ethylene/vinyl alcohol copolymer. In some embodiments, tie layers can comprise at least one member selected from the group including, but not limited to, modified polyolefin, modified ethylene/vinyl acetate copolymer, and/or homogeneous ethylene/alpha-olefin copolymer. In some embodiments, tie layers can comprise at least one member selected from the group consisting of anhydride modified grafted linear low density polyethylene, anhydride grafted low density polyethylene, homogeneous ethylene/alpha-olefin copolymer, and/or anhydride grafted ethylene/vinyl acetate copolymer.

Any direction referred to herein, such as "top," "bottom," "left," "right," "upper," "lower," and other directions and orientations are described for clarity in reference to the figures and are not to be limiting. It is to be understood that the films or systems described herein can be used in a wide variety of directions and orientations.

All compositional percentages used herein are presented on a "by weight" basis, unless designated otherwise.

Although the majority of the above definitions are substantially as understood by those of skill in the art, one or more of the above definitions can be defined hereinabove in a manner differing from the meaning as ordinarily understood by those of skill in the art, due to the particular description herein of the presently disclosed subject matter.

III. The Presently Disclosed Film

III.A. Generally

The presently disclosed subject matter is directed to a polymeric film suitable for use in a wide variety of applications, such as (but not limited to) the formation of bioprocessing containers. Particularly, the disclosed film includes a first barrier layer comprising polyglycolic acid (PGA), polyamide, ethylene vinyl alcohol (EVOH), and/or an EVOH blend and a second barrier layer comprising EVOH to ensure high gas barrier under a variety of conditions. In addition, the disclosed film is biologically inert and is free from surface-modifying additives to ensure that the film does not inhibit the growth of biological cell cultures.

The first and second barrier layers ensure that the disclosed films maintain gas barrier properties under a wide variety of conditions—i.e., low, intermediate, and high relative humidity. Particularly, in some embodiments, the disclosed film exhibits an oxygen transmission rate (OTR) after at least one hour in high, intermediate, or low relative humidity conditions of about 0 to 500 cc/m$^2$/atm/day; in some embodiments, about 0 to 300 cc/m$^2$/atm/day; and in some embodiments, about 0 to 200 cc/m$^2$/atm/day. OTR refers to the rate of oxygen gas passing through a film structure and can be measured according to ASTM D-3985.

The disclosed film comprises two or more layers to incorporate a variety of properties, such as sealability, gas impermeability, and toughness into a single film. Thus, in some embodiments, the disclosed film comprises a total of from about 2 to about 20 layers; in some embodiments, from about 3 to about 12 layers; and in some embodiments, from about 4 to about 9 layers. Accordingly, the disclosed film can comprise 2, 3, 4, 5, 6, 7, 8, 9, 10, 11, 12, 13, 14, 15, 16, 17, 18, 19, or 20 layers. One of ordinary skill in the art would also recognize that the disclosed film can comprise more than 20 layers, such as in embodiments wherein the film components comprise microlayering technology.

The disclosed film can be constructed using any suitable process known to those of ordinary skill in the art, including (but not limited to) coextrusion, lamination, extrusion coating, and combinations thereof. See, for example, U.S. Pat. No. 6,769,227 to Mumpower; U.S. Pat. No. 3,741,253 to Brax et al.; U.S. Pat. No. 4,278,738 to Brax et al.; U.S. Pat. No. 4,284,458 to Schirmer; and U.S. Pat. No. 4,551,380 to Schoenberg, each of which is hereby incorporated by reference in its entirety.

The disclosed film can have any total thickness desired, so long as the film provides the desired properties for the particular packaging operation in which the film is used, e.g., optics, modulus, seal strength, and the like. Final web thicknesses can vary, depending on processing, end use application, and the like. Typical thicknesses can range from about 0.1 to 20 mils; in some embodiments, about 0.3 to 15 mils; in some embodiments, about 0.5 to 10 mils; in some embodiments, about 1 to 8 mils; in some embodiments, about 1 to 4 mils; and in some embodiments, about 1 to 2 mils. Thus, in some embodiments, the film can have a thickness of about 10 mils or less; in some embodiments, a thickness of about 5 mils or less. One of ordinary skill in the art would also recognize that the presently disclosed subject matter also includes embodiments wherein films lie outside the ranges set forth herein.

In some embodiments, the disclosed film can comprise printed product information such as (but not limited to) product size, type, name of manufacturer, instructions for use, and the like. Such printing methods are well known to those of ordinary skill in the packaging art.

In some embodiments, the disclosed film is biologically inert (i.e., compatible with cell culture). Particularly, the disclosed film is substantially free of surface-modifying additives (i.e., the total absence of or near total absence of a surface-modifying additive). In some embodiments, the term "substantially free" refers to about 5% (by weight) or less; in some embodiments, about 4% or less; in some embodiments, about 3% or less; in some embodiments, about 2% or less; and in some embodiments, about 1% or less surface-modifying additives, based on the total weight of the film. Surface-modifying additives are well known to those of ordinary skill in the art and can include (but are not limited to) protein coatings, therapeutic agent coatings, binding agents, and the like.

III.B. Sealant Layer

As set forth herein, the disclosed multilayer film comprises a first barrier layer positioned adjacent to a sealant layer. The sealant layer comprises an olefin hydrocarbon polymer with glass transition temperature ("$T_g$") greater than or equal to 25° C. (in accordance with ASTM D-3418) and an alpha-olefin copolymer. Suitable olefin hydrocarbon polymers can include polymers prepared by the polymerization of vinyl monomers, particularly styrene, acrylonitrile, vinyl chloride, vinylidene chloride, and the like, as well as the various acrylates, methacrylates, acrylamides, and their derivatives, so long as the vinyl polymer exhibits a Tg greater than or equal to 25° C. For example, in some embodiments, the olefin hydrocarbon polymer can be selected from the group comprising: cyclic olefin copolymer, cyclic olefin homopolymer, poly(3-methyl-1-butene), poly(4-methyl-1-pentene), poly(3,3-dimethyl-1-butene), poly(4,4-dimethyl-1-pentene), poly(vinyl t-butyl ether), polystyrene, and combinations thereof.

In some embodiments, suitable alpha olefin copolymers can include heterogeneous materials, such as linear low density polyethylene (LLDPE) with a density usually in the range of from about 0.915 g/cm$^3$ to about 0.930 g/cm$^3$, linear medium density polyethylene (LMDPE) with a density usually in the range of from about 0.930 g/cm$^3$ to about 0.945 g/cm$^3$, and very low and ultra low density polyethylene (VLDPE and ULDPE) with a density lower than about 0.915 g/cm$^3$. Suitable alpha-olefin copolymers can in some embodiments include homogeneous polymers, such as metallocene-catalyzed EXACT® and EXCEED® homogeneous resins obtainable from Exxon, single-site AFFINITY® resins obtainable from Dow, and TAFMER® homogeneous ethylene-alpha-olefin copolymer resins obtainable from Mitsui. All these materials generally include co-polymers of ethylene with one or more co-monomers selected from (C4-C10)-alpha-olefin such as butene-1, hexene-1, octene-1, etc., in which the molecules of the copolymers include long chains with relatively few side chain branches or cross-linked structures.

In some embodiments, the sealant layer can comprise about 5-95 weight percent olefin hydrocarbon polymer and 95-5 weight percent alpha olefin copolymer; in some embodiments, about 5-75 weight percent olefin hydrocarbon polymer and about 25-95 weight percent alpha olefin copolymer; in some embodiments, about 5-55 weight percent olefin hydrocarbon polymer and about 45-95 weight percent alpha olefin copolymer; in some embodiments, about 5-35 weight percent olefin hydrocarbon polymer and about 65-95 weight percent alpha olefin copolymer; in some embodiments, about 10-30 weight percent olefin hydrocarbon polymer and about 70-90 weight percent alpha olefin copolymer; and in some embodiments, about 15-25 weight percent olefin hydrocarbon polymer and about 75-85 weight percent alpha olefin copolymer, based on the total weight of the layer. Thus, in some embodiments, the sealant layer can comprise about 20 weight percent olefin hydrocarbon polymer and about 80 weight percent alpha olefin copolymer, based on the total weight of the layer.

III.C. First Barrier Layer

The disclosed film includes a first barrier layer comprising PGA, polyamide, EVOH and/or an EVOH blend positioned adjacent to the sealant layer (i.e., towards the packaged product). PGA is a known polymeric material and can be prepared using any of a wide variety of methods known in the art. For example, in some embodiments, PGA can be prepared using the ring-opening polymerization of glycolide using stannous octoate catalyst (D. K. Gilding and A. M. Reed in Polymer, Vol. 20, p. 1459 (1979)). Alternatively, in some embodiments, PGA can be produced by a process such as dehydration polycondensation of glycolic acid, dealcoholization polycondensation of an alkyl glycolate, desalting polycondensation of a glycolic acid salt, and/or ring-opening polymerization of glycolide.

Polyamides are known in the art and include polymers having amide linkages (such as synthetic polyamides) and can be either aliphatic or aromatic and either in semi-crystalline or amorphous form. Suitable polyamides can include both polyamides and co-polyamides. In some embodiments, suitable polyamides can be selected from nylon compounds approved for use in producing articles intended for use in processing, handling, and packaging, including the homopolymers, copolymers, and mixtures of the nylon materials described in 21 C.F.R. 177.1500 et seq., incorporated herein in its entirety.

For example, exemplary polyamides can include (but are not limited to) nylon homopolymers and copolymers such as those selected from the group comprising: nylon 4,6 (poly(tetramethylene adipamide)), nylon 6 (polycaprolactam), nylon 6,6 (poly(hexamethylene adipamide)), nylon 6,9 (poly(hexamethylene nonanediamide)), nylon 6,10 (poly(hexamethylene sebacamide)), nylon 6,12 (poly(hexamethylene dodecanediamide)), nylon 6/12 (poly(caprolactam-co-laurallactam)), nylon 6,6/6 (poly(hexamethylene adipamide-co-caprolactam)), nylon 6/66 (poly(caprolactam-co-hexamethylene adipamide)), nylon 66/610 (e.g., manufactured by the condensation of mixtures of nylon 66 salts and nylon 610 salts), nylon 6/69 resins (e.g., manufactured by the condensation of epsilon-caprolactam, hexamethylenediamine and azelaic acid), nylon 11 (polyundecanolactam), nylon 12 (polyauryllactam), nylon MXD6, nylon MXDI, nylon 6I/6T, and copolymers or mixtures thereof.

In some embodiments, the disclosed film comprises a first barrier layer comprising neat EVOH or a blend of two or more EVOHs. As would be known to those of ordinary skill in the art, EVOH is a copolymer consisting essentially of ethylene and vinyl alcohol recurring structural units and can contain small amounts of other monomer units, such as vinyl ester units. EVOH can be prepared by saponification, partial alcoholysis of ethylene-vinyl ester copolymers, and/or complete alcoholysis of ethylene-vinyl ester copolymers.

The molar proportion of ethylene in an EVOH suitable for use in the first barrier layer can range from about 3 mol % to about 75 mol %; in some embodiments, from about 10 mol % to about 50 mol %; in some embodiments, from about 20 mol % to about 52 mol %; and in some embodiments, from about 23 mol % to about 48 mol %. Thus, the molar proportion of ethylene in the EVOH can be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 mol %. However, greater or lesser amounts of ethylene content are also envisioned and can be included within the scope of the presently disclosed subject matter.

In some embodiments, the first barrier layer can comprise neat (about 100 weight percent, based on the total weight of the layer) PGA, neat EVOH, a blend of at least two EVOHs, neat polyamide, or a PGA/polyamide blend. In embodiments comprising a PGA/polyamide blend, the blend can comprise up to about 50% PGA and at least about 50% polyamide. Thus, in some embodiments, the blend can include about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 weight percent PGA, based on the total weight of the layer. Accordingly, in some embodiments, the blend can comprise about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 weight percent polyamide, based on the total weight of the layer.

III.D. Second Barrier Layer

As set forth herein above, the disclosed film comprises a second barrier layer comprising neat EVOH or an EVOH blend, positioned adjacent to the skin layer (i.e., towards the outside of the package). As set forth above, EVOH is a copolymer consisting essentially of ethylene and vinyl alcohol recurring structural units and can contain small amounts of other monomer units, such as vinyl ester units. EVOH can be prepared by saponification, partial alcoholysis of ethylene-vinyl ester copolymers, and/or complete alcoholysis of ethylene-vinyl ester copolymers.

The molar proportion of ethylene in an EVOH suitable for use in the second barrier layer can range from about 3 mol % to about 75 mol %; in some embodiments, from about 10 mol % to about 50 mol %; in some embodiments, from about 20 mol % to about 52 mol %; and in some embodiments, from about 23 mol % to about 48 mol %. Thus, the molar proportion of ethylene in the EVOH can be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 mol %. However, greater or lesser amounts of ethylene content are also envisioned and can be included within the scope of the presently disclosed subject matter.

III.E. Skin Layer

In some embodiments, the disclosed film includes a skin layer comprising polyethylene terephthalate (PET) or blends of PET wherein at least one PET in the blend is amorphous and has Tg≥50° C. (in accordance with ASTM D-3418). As would be known in the art, PET includes polymers that contain ethylene units and include, based on the dicarboxylate units, at least 90 mol % of terephthalate units. The remaining monomer units are selected from other dicarboxylic acids or diols. Amorphous PET (or "APET") refers to a poly(ethylene terephthalate) material that has a low degree of crystallinity, typically about 5 to 10%.

Alternatively, in some embodiments, the disclosed film comprises a skin layer comprising polyamide or blends of polyamide, wherein at least one polyamide in the blend is amorphous and has Tg≥50° C. Amorphous polyamides are well known to those skilled in the art. Specifically, amorphous polyamides include polyamides that are lacking in crystallinity as shown by the lack of an endotherm crystalline melting peak in a Differential Scanning calorimeter ("DSC") measurement (ASTM D-3417), 10° C./minute heating rate.

In some embodiments, the polyamide of the skin layer can comprise any of a wide variety of elastomeric polyamides, as would be known to those of ordinary skill in the art. For example, suitable elastomeric polyamides can include (but are not limited to) Vestamid® E40-53, Vestamid® L1670, Vestamid® D16 (all 3 available from Evonik Corp., Leesport, Pa., United States of America), Grilamid® ELY20NZ, Grilamid® 2702, Grilamid® 2475, and Grilamid® 60 (all 4 available from EMS Grivory, Domat, Switzerland).

III.F. Additional Layers

In some embodiments, the disclosed film can comprise at least one abuse layer. The abuse layer can be any film layer, so long as the film layer serves to resist abrasion, puncture, or other potential causes of reduction of package and/or container integrity or package/container appearance quality.

In some embodiments, the presently disclosed film can comprise at least one bulk layer that functions to increase the abuse resistance, toughness, and/or modulus of the film.

In some embodiments, the disclosed film can comprise one or more tie layers adapted for improving the adherence of one layer of said film to another layer.

Various combinations of layers can be used in the formation of a multilayer film in accordance with the presently disclosed subject matter. For example, in some embodiments, the disclosed film can comprise the following combination A/B/C/B/D, where A represents a sealant layer; B represents a barrier layer (such as the first and second barrier layers disclosed herein), C represents a core layer (which can be a bulk layer or an abuse layer); and D represents a skin layer. One or more tie layers (T) can optionally be used between any one or more layers of the above multilayer film structures (i.e., A/T/B/T/C/T/B/T/D). Further, one or more abuse (E) and/or bulk layers (F) can be used in between any one or more layers of the above multilayer film structures, as would be known to those of ordinary skill in the art.

Regardless of the film structure, the disclosed film and/or layers can include other additives commonly used in the art. For example, in some embodiments, such additives can include (but are not limited to) thermal stabilizers, lubricating aids, processing aids, slip agents, antiblock agents, and/or pigments. In some embodiments, the amount of additives present in the film is minimized such that the film properties are not deteriorated.

IV. Methods of Using the Disclosed Film

While the disclosed films can have applications in a wide variety of areas, in some embodiments, they can be suitable for use in constructing bioprocessing containers for cell culturing applications. The presently disclosed bioprocessing containers provide a flexible, disposable environment for culturing cells, cell aggregates, particles, tissues, and the like. The cell culture bags can be stand-alone or can be used with a wide variety of support devices, such as bioreactors, stirred tank reactors, and the like.

A suitable culture container can include a body constructed from first and second flexible sidewalls sealed along their edges to define an inner containment area for housing a product. The first and/or second sidewalls can be constructed from the disclosed dual barrier film. In some embodiments, the film can be used by itself or with a non-barrier film to form a double wall container constructed from multiple film plies sealed together around the container perimeter. In these embodiments, the inner and/or outer film plies can comprise the barrier layers. Double walled containers are popular in bioprocessing applications due to the increase in abuse resistance properties and are well known to those of ordinary skill in the art.

In some embodiments, to provide a cell growth surface, the interior surface of the container can be treated by any of a wide variety of methods known in the art, including (but not limited to) plasma discharge, corona discharge, gas plasma discharge, ion bombardment, ionizing radiation, and/or high intensity UV light.

In some embodiments, the disclosed container can be pre-sterilized prior to the introduction of biological materials (i.e., cells). As most cell culture procedures are carried out under aseptic conditions by practicing sterile technique, the pre-sterilization of the bioprocessing container allows the culture chamber and the fluid pathway to be maintained in a sterile, closed environment. For example, the disclosed containers can in some embodiments be sterilized by exposure to gamma radiation, ultraviolet radiation, ethylene oxide, or combinations thereof, as would be known to those of ordinary skill in the art. After the bioprocessing container has been sterilized, an appropriate liquid medium can be deposited into the interior of the container, depending on the particular use desired. For example, cell culture medium can be deposited into the container interior to grow a cell culture. The container can then be inoculated and incubated as would be known to those of ordinary skill in the art.

The disclosed bioprocessing container can be configured such that the contents housed therein remain substantially in contact only with the container during use. In such embodiments, the container can be disposable and used for a single reaction or a single series of reactions, after which the container is discarded. Because the liquid in the collapsible container in such embodiments does not come into contact with a support structure (if used), the support structure can be reused without cleaning. That is, after a reaction takes place in the flexible container, it can be removed from the support structure and replaced by a second (e.g., disposable) container. A second reaction can be carried out in the second container without cleaning/sterilizing the first container and/or the reusable support structure.

The disclosed flexible containers can include at least one access port whereby cells and/or cell culture media can be introduced and/or removed. In some embodiments, a syringe or other transport device can be used to introduce materials into the container interior through the access port. It should be appreciated that any number of access ports can be provided in accordance with the disclosed bioprocessing container. For example, in some embodiments, the container can have an access port that functions as an inlet for the introduction of items into the container interior and a separate access port that functions as an outlet. The access port(s) can be equipped with suitable measures for sealing against leakage, such as valves and the like, as would be conventionally known.

In some embodiments, the disclosed container can include one or more gas removal ports. In some embodiments, the gas removal port can transverse both sides of the container and can be fused to the container sidewall. In some embodiments, the gas removal port can include an internal gasket and an external gasket to ensure that there is no leakage around the port where it protrudes through the container. As would be appreciated by those of ordinary skill in the art, the access port can function as the gas removal port in some embodiments.

In some embodiments, the disclosed flexible container can comprise one or more sampling ports that can be used for sampling, analyzing (e.g., determining pH and/or amount of dissolved gases in the liquid), or for other purposes. The sampling ports can be aligned with the one or more access ports of the container. It should be understood that the sampling ports are optional, and that in some embodiments sampling can be accomplished through the access port.

In some embodiments, the bioprocessing container can optionally include a mixing system, such as a pulsating disk, paddle mixer, rocking platform, impeller, and the like. For example, in some embodiments, the container (and optionally a container support assembly) can be rotated about one axis (such as, for example, the longitudinal axis) of the container. However, the container support assembly and/or the enclosed container can be tilted and rotated at an angle from the longitudinal axis of the container support assembly. Alternatively or in addition, in some embodiments, the disclosed container can include a mixing system (such as an impeller) positioned within the interior of the container. The impeller can be rotated using a motor that can be external or internal to the container.

In some embodiments, the disclosed container can optionally include a heater, such as (but not limited to) a heating pad, a steam jacket, a circulating fluid heater, and/or a water heater. The heater can be located between the container and a support housing or the heater can be incorporated into the housing or container itself. In some embodiments, the bioprocessing container can be placed inside an incubator to maintain a desired temperature.

The shape of the flexible container can be determined by the size and shape of the container support assembly (if any) to be used. It should be noted that the disclosed containers can have any of a wide variety of shapes known in the art. To this end, the length and/or diameter of the container can be scaled to any desired and suitable size depending on the particular use. For example, the container can have a volume of about 1-40, 40-100, 100-200, 200-300, 300-500, 500-750, 750-1000, 1000-2000, 2000-5000, or 5000-10000 liters. Thus, in some embodiments, the disclosed container has a volume greater than 1, 10, 20, 40, 100, 200, 500, or 1,000 liters. Volumes less than 1 liter and greater than 10,000 liters are also possible and are included within the scope of the presently disclosed subject matter.

The disclosed container is suitable for any of a wide variety of bioprocessing applications including (but not limited to) cell culturing of prokaryotic or eukaryotic cells, culturing of complex tissues and organs, and similar applications as would be well known in the art. For example, in some embodiments, cell culture medium is added to the interior compartment of the container and is then inoculated with a cell culture.

Thus, any of a wide variety of cells, tissues, and the like can be grown, including but not limited to primary cell cultures, immortalized cell cultures, cultured cells, organs, tissues, etc. In some embodiments, the cell culture can be inoculated with cells prior to adding to the container interior. In these embodiments, the cell culture medium is pre-inoculated and then added to the interior compartment of the bioprocessing container. Once the culture medium and cells have been deposited into the interior compartment, the cells can be incubated within the interior of the container under conditions suitable for cell growth (i.e., temperature, agitation, and the like). Suitable conditions for each particular cell type are well known to those of ordinary skill in the art or can be ascertained using routine experimentation.

V. Advantages of the Disclosed Film

In some embodiments, the disclosed film can be used to construct a flexible and disposable container for a variety of purposes, including media preparation, buffer preparation, storage of cell products, culturing cells, culturing microorganisms, culturing plant metabolites, processing foods, processing chemicals, processing biopharmaceuticals, processing biologicals, and the like. The disposable bioprocessing container assembly allows a user to operate the culture or production with relative ease and little training.

The disposable system disclosed herein does not require cleaning or sterilizing after use, thereby preserving user time and resources.

In addition, the disclosed film can be used to provide an improved cell culture container for growing cells in vitro. Specifically, the disclosed film lacks cell surface modifiers that can interfere with cell culture techniques. The disclosed film also provides a barrier feature to the disclosed bioprocessing containers in low, medium, and high relative humidity conditions.

Although several advantages of the disclosed system are set forth in detail herein, the list is by no means limiting. Particularly, one of ordinary skill in the art would recognize that there can be several advantages to the disclosed film and methods that are not included herein.

EXAMPLES

The following Examples provide illustrative embodiments. In light of the present disclosure and the general level of skill in the art, those of ordinary skill in the art will appreciate that the following Examples are intended to be exemplary only and that numerous changes, modifications, and alterations can be employed without departing from the scope of the presently disclosed subject matter.

Several film structures in accordance with the presently disclosed subject matter and comparatives are identified herein below in Tables 1 and 2.

TABLE 1

| Resin Identification | | |
|---|---|---|
| Material Code | Trade Name or Designation | Source |
| A | 8007F-400 | Topas Advanced Polymers, Inc. (Florence, Kentucky, United States of America) |
| B | EXCEED ® 2718CB | ExxonMobile (Fairfax, Virginia, United States of America) |
| C | TYMOR ® 1228B | Dow Chemical Company (Midland, Michigan, United States of America) |
| D | Kuredux ® 100R60 | Kureha Corporation (Tokyo, Japan) |
| E | Ultramid ® B40 | BASF Corporation (Florham Park, New Jersey, United States of America) |
| F | Grivory ® G21 Natural | EMS-Grivory (Domat, Switzerland) |
| G | SOARNOL ® SGN017 | Nippon Gohsei (Tokyo, Japan) |
| H | SOARNOL ® AT4403 | Nippon Gohsei (Tokyo, Japan) |
| I | SOARNOL ® ET3803 | Nippon Gohsei (Tokyo, Japan) |
| J | SOARNOL ® SG654B | Nippon Gohsei (Tokyo, Japan) |
| L | Texin ® SUN-3006 | Bayer Material Science AG (Leverkusen, Germany) |

TABLE 1-continued

Resin Identification

| Material Code | Trade Name or Designation | Source |
|---|---|---|
| M | Texin ® 3044 | Bayer Material Science AG (Leverkusen, Germany) |
| N | Texin ® 285 | Bayer Material Science AG (Leverkusen, Germany) |
| O | Texin 990 | Bayer Material Science AG (Leverkusen, Germany) |
| P | AMPLIFY ® TY 1451 | Dow Chemical Company (Midland, Michigan, United States of America) |
| Q | AFFINITY ® EG 8100G | Dow Chemical Company (Midland, Michigan, United States of America) |
| R | BYNEL ® 21E810 | E.I. DuPont de Nemours and Company (Wilmington, Delaware, United States of America) |
| S | Ecdel ® 9965 | Eastman Chemical Company (Kingsport, Tennessee, United States of America) |
| T | SYLOID ® 74X6000 | Grace Davison (Deerfield, Illinois, United States of America) |
| U | EASTAR ® 6763 C0235 | Eastman Chemical Company (Kingsport, Tennessee, United States of America) |
| V | Pebax ® 1205 sA 01 | Arkema (Colombes, France) |
| W | IRGANOX ® 1010 | BASF Corporation (Florham Park, New Jersey, United States of America) |
| X | Tuflin ® HS-7001 NT 7 | Dow Chemical Company (Midland, Michigan, United States of America) |
| Y | Tritan ® MP100 | Eastman Chemical Company (Kingsport, Tennessee, United States of America) |
| Z | Admer ® SF755A | Mitsui Petrochemical Corporation (New York, New York, United States of America) |
| AA | Ader SF730E | Mitsui Petrochemical Corporation (New York, New York, United States of America) |
| BB | CV77518 | Westlake Chemical Corporation (Houston, Texas, United States of America) |
| CC | MXD S7007 | Mitsubishi Gas Chemical (New York, New York, United States of America) |
| DD | Topas ® E-140 | Topas Advanced Polymers, Inc. (Florence, Kentucky, United States of America) |
| EE | Soarnal ® ST1304B | Nippon Gohsei (Tokyo, Japan) |
| FF | PLEXAR ® PX3227 | Nippon Gohsei (Tokyo, Japan) |
| GG | CV77528 | Westlake Chemical Corporation (Houston, Texas, United States of America) |
| HH | XUS 61520.15L | Dow Chemical Company (Midland, Michigan, United States of America) |
| II | Kraton ® G1657 | Kraton Polymers (Houston, Texas, United States of America) |
| JJ | EXCEED ® 1012CJ | ExxonMobile (Fairfax, Virginia, United States of America) |
| KK | Kraton ® G1730 | Kraton Polymers (Houston, Texas, United States of America) |
| LL | Hybrar ® 7125 | Kuraray Europe GMBH (Nuremberg, Germany) |
| MM | MB50-313 | Dow Corning Silicones (Midland, Michigan, United States of America) |
| NN | Hytrel ® 3078 | E.I. DuPont de Nemours and Company (Wilmington, Delaware, United States of America) |
| OO | W0038-081 | Westlake Chemical Corporation (Houston, Texas, United States of America) |
| PP | W00038-034 | Westlake Chemical Corporation (Houston, Texas, United States of America) |
| QQ | SP2403 | Westlake Chemical Corporation (Houston, Texas, United States of America) |
| RR | Modic ® x3043K | Mitsubishi Gas Chemical (New York, New York, United States of America) |
| SS | Ampacet 10768 | Ampacet (Tarrytown, New York, United States of America) |
| TT | ULTRAMID ® C33 01 | BASF Corporation (Florham Park, New Jersey, United States of America) |
| UU | ULTRAMID ® B33LN 01 | BASF Corporation (Florham Park, New Jersey, United States of America) |
| XX | Ecdel ® 9966 | Eastman Chemical Company (Kingsport, Tennessee, United States of America) |
| YY | Zeonor ® 1060R | Zeon Chemicals, LP (Louisville, Kentucky, United States of America) |
| AAA | BYNEL ® CXA 21E787 | E.I. DuPont de Nemours and Company (Wilmington, Delaware, United States of America) |
| BBB | Vestamid ® E40-53 | Evonik Corp. (Leesport, Pennsylvania, United States of America) |
| CCC | Vestamid ® L1670 | Evonik Corp. (Leesport, Pennsylvania, United States of America) |

TABLE 1-continued

Resin Identification

| Material Code | Trade Name or Designation | Source |
|---|---|---|
| DDD | Vestamid ® D16 | Evonik Corp. (Leesport, Pennsylvania, United States of America) |

A is ethylene/norbornene copolymer with density of 1.02 g/cm$^3$, melt volume flow rate of 0.122 in$^3$/10 min., and glass transition temperature (DSC) of 80° C.
B is linear low density ethylene/hexene copolymer with density of 0.918 g/cc and DSC melt temperature of 115° C.
C is linear low density maleic anhydride-modified polyethylene with density of 0.921 g/cc, melt point of 123° C. (ASTM D-1505), and vicat softening point of 104° C. (ASTM D-1525).
D is homopolymer polyglycolic acid (PGA) resin of 200,000 g/mol and Mw/Mn of 1.9.
E is polyamide 6 with specific gravity of 1.13, relative viscosity 3.98-4.19 (sulfuric acid), and DSC melting point 220° C.
F is amorphous nylon copolymer (6I/6T) with density of 1.16-1.20 g/cc, melt flow rate of 90 MI/10 minutes, glass transition temperature of 125° C., and relative viscosity of 1.49-1.56.
G is hydrolyzed ethylene/vinyl acetate copolymer (27 mol % ethylene).
H is hydrolyzed ethylene/vinyl acetate copolymer (44 mole % ethylene) with flow rate of 3.5 g/10 min., density of 1/14 g/cc, and DSC melting point of 164° C.
I is hydrolyzed ethylene/vinyl acetate copolymer (36.5-39.5 mole % ethylene) with flow rate of 2.9-3.5 g/10 minutes, density of 1.17 g/cc, melting point (DSC) of 173° C., and glass transition temperature (DSC) of 58° C.
J is hydrolyzed ethylene/vinyl acetate copolymer (36.5-39.5 mole % ethylene) with density of 1.17 g/cc, melting point (DSC) 173° C., and glass transition temperature of 58° C.
L is aliphatic polyether-based thermoplastic polyurethane with specific gravity (ASTM D-792) of 1.08, glass transition temperature of −40° C., and softening temperature of 109° C.
M is aliphatic polyester-based thermoplastic polyurethane with specific gravity (ASTM D-792) of 1.13, glass transition temperature of −20° C., and vicat softening temperature (ASTM D-1525) of 39° C.
N is aromatic polyester-based thermoplastic polyurethane with specific gravity (ASTM D-792) of 1.20, shore hardness (ASTM D-2240) of 85A, and glass transition temperature of −42° C.
O is polyether-based thermoplastic polyurethane with glass transition temperature of −47° F. and specific gravity (ASTM D-792) of 1.13.
P is maleic anhydride-modified polyethylene with flow rate of 1.4 g/10 min. (ASTM 1238) and density of 0.908 g/cc.
Q is very low density ethylene/octene copolymer with flow rate (Condition E) of 0.75-1.25 g/10 min. and density of 0.867-0.873 g/cc.
R is maleic anhydride-modified ethylene/methyl acrylate copolymer with flow rate of 2.9 g/10 min. and density of 0.931 g/cc.
S is copolyester with DSC melting point of 195-215° C. and density of 1.13 g/cc.
T is amorphous silica with density of 2.1 g/cc.
U is silica in polyethylene terephthalate/glycol with density of 1.29 g/cc (ASTM D-1928).
V is polyether copolyamide with density of 1.01 g/cc and melting point of 147° C.
W is phenolic antioxidant.
X is linear low density ethylene/hexene copolymer with density of 0.917 and melt index of 3.2.
Y is amorphous copolyester with Tg of 110° C. and density of 1.19 g/cc.
Z is anhydride-modified ethylene acrylate.
AA is very low density maleic anhydride-modified polyethylene.
BB is linear low density ethylene/hexene copolymer with density of 0.91 g/cc.
CC is MXD6/MXDI polyamide.
DD is cyclic olefin copolymer.
EE is hydrolyzed ethylene/vinyl acetate copolymer.
FF is maleic anhydride-modified linear low density polyethylene, with melt index of 1.3-2.1 g/min., density of 0.909-0.917 g/cc, vicat softening point of 82° C., and melting point of 124° C.
GG is linear low density ethylene/hexene copolymer with melt index of 1.7-2.3 dg/min. and density of 0.908-0.912 g/cc.
HH is very low density ethylene/octene copolymer with flow rate of 0.50 (+/−0.15) g/10 min., density of 0.901-0.905 g/cc, and DSC melting temperature of 123° C.
II is styrene/ethylene/butene terpolymers.
JJ is very low density ethylene/hexene copolymer with density of 0.910-0.914 g/cc and melt flow rate of 0.8-1.2 g/10 min.
KK is polystyrene copolymer.
LL is styrene/butadiene/styrene triblock copolymer.
MM is 47-53 weight percent polydimethylsiloxane in linear low density polyethylene with density of 0.94 g/cc.
NN is elastomeric polyester with DSC melting point of 195-215° C. and density of 1.13 g/cc.
OO is maleic anhydride-modified linear low density polyethylene.
PP is very low density polyethylene.
QQ is ethylene/methyl acrylate copolymer (24 weight % MA) with density of 0.944 g/cc and melt index 2.1 g/10 min.
RR is anhydride-modified ethylene acrylate.
SS is Irgatos ® 168 in LDPE.
TT is polyamide 6/66 with DSC melting point of 190-202° C. and density of 1.10-1.161 g/cc.
UU is polyamide-6 with specific gravity of 1.135-1.145 and DSC melting point of 210-230° C.
XX is copolyester.
YY is cyclic olefin homopolymer.
AAA is maleic anhydride-modified ethylene/methyl acrylate copolymer with 0.16-0.26 weight percent maleic anhydride, density of 0.90-0.96 g/cc, DSC melting temperature of 92° C., and vicat softening point of 52° C.
BBB is polyamide-12 elastomer that consists of blocks of polyamide-12 crystalline hard segments and polyether soft segments.
CCC is polyamide-12.
DDD is polyamide 6/12.

TABLE 2

Film Identification

| Film ID | Layer | Formulation | Volume % | Mils |
|---|---|---|---|---|
| Film 1 | 1 | 65% A / 35% B | 27.3 | 3.0 |
| | 2 | 100% C | 4.5 | 0.5 |
| | 3 | 100% D | 4.5 | 0.5 |
| | 4 | 100% C | 4.5 | 0.5 |
| | 5 | 100% B | 36.4 | 4.0 |
| | 6 | 100% C | 4.5 | 0.5 |
| | 7 | 100% D | 4.5 | 0.5 |
| | 8 | 100% C | 4.5 | 0.5 |
| | 9 | 80% E / 20% F | 9.1 | 1.0 |
| Film 2 | 1 | 65% A / 35% B | 27.3 | 3.0 |
| | 2 | 100% C | 4.5 | 0.5 |
| | 3 | 100% D | 4.5 | 0.5 |
| | 4 | 100% C | 4.5 | 0.5 |
| | 5 | 100% B | 36.4 | 4.0 |
| | 6 | 100% C | 4.5 | 0.5 |
| | 7 | 75% G / 25% H | 4.5 | 0.5 |
| | 8 | 100% C | 4.5 | 0.5 |
| | 9 | 80% E / 20% F | 9.1 | 1.0 |
| Film 3 | 1 | 65% A / 35% B | 27.3 | 3.0 |
| | 2 | 100% C | 4.5 | 0.5 |
| | 3 | 100% D | 4.5 | 0.5 |
| | 4 | 100% C | 4.5 | 0.5 |
| | 5 | 100% B | 36.4 | 4.0 |
| | 6 | 100% C | 4.5 | 0.5 |
| | 7 | 100% G | 4.5 | 0.5 |
| | 8 | 100% C | 4.5 | 0.5 |
| | 9 | 80% E / 20% F | 9.1 | 1.0 |
| Film 4 | 1 | 65% A / 35% B | 27.3 | 3.0 |
| | 2 | 100% C | 4.5 | 0.5 |
| | 3 | 100% D | 4.5 | 0.5 |
| | 4 | 100% C | 4.5 | 0.5 |
| | 5 | 100% B | 36.4 | 4.0 |
| | 6 | 100% C | 4.5 | 0.5 |
| | 7 | 100% I | 4.5 | 0.5 |
| | 8 | 100% C | 4.5 | 0.5 |
| | 9 | 80% E / 20% F | 9.1 | 1.0 |
| Film 5 | 1 | 65% DD / 35% B | 27.3 | 3.0 |
| | 2 | 100% C | 4.5 | 0.5 |
| | 3 | 100% D | 4.5 | 0.5 |
| | 4 | 100% C | 4.5 | 0.5 |
| | 5 | 100% B | 36.4 | 4.0 |
| | 6 | 100% C | 4.5 | 0.5 |
| | 7 | 100% I | 4.5 | 0.5 |
| | 8 | 100% C | 4.5 | 0.5 |
| | 9 | 80% E / 20% F | 9.1 | 1.0 |
| Film 6 | 1 | 65% A / 35% B | 27.3 | 3.0 |
| | 2 | 100% C | 4.5 | 0.5 |
| | 3 | 100% I | 4.5 | 0.5 |
| | 4 | 100% C | 4.5 | 0.5 |
| | 5 | 100% B | 36.4 | 4.0 |
| | 6 | 100% C | 4.5 | 0.5 |
| | 7 | 100% I | 4.5 | 0.5 |
| | 8 | 100% C | 4.5 | 0.5 |
| | 9 | 80% E / 20% F | 9.1 | 1.0 |
| Film 7 | 1 | 65% A / 35% B | 27.3 | 3.0 |
| | 2 | 100% C | 4.5 | 0.5 |
| | 3 | 100% J | 4.5 | 0.5 |
| | 4 | 100% C | 4.5 | 0.5 |
| | 5 | 100% B | 36.4 | 4.0 |
| | 6 | 100% C | 4.5 | 0.5 |
| | 7 | 100% J | 4.5 | 0.5 |
| | 8 | 100% C | 4.5 | 0.5 |

TABLE 2-continued

Film Identification

| Film ID | Layer | Formulation | Volume % | Mils |
|---|---|---|---|---|
| | 9 | 80% E / 20% F | 9.1 | 1.0 |
| Film 8 | 1 | 65% A / 35% B | 27.3 | 3.0 |
| | 2 | 100% C | 4.5 | 0.5 |
| | 3 | 100% J | 4.5 | 0.5 |
| | 4 | 100% C | 4.5 | 0.5 |
| | 5 | 100% B | 36.4 | 4.0 |
| | 6 | 100% C | 4.5 | 0.5 |
| | 7 | 100% J | 4.5 | 0.5 |
| | 8 | 100% C | 4.5 | 0.5 |
| | 9 | 80% E / 20% F | 9.1 | 1.0 |
| Film 9 | 1 | 65% A / 35% B | 27.3 | 3.0 |
| | 2 | 100% C | 4.5 | 0.5 |
| | 3 | 100% I | 4.5 | 0.5 |
| | 4 | 100% C | 4.5 | 0.5 |
| | 5 | 100% L | 36.4 | 4.0 |
| | 6 | 100% C | 4.5 | 0.5 |
| | 7 | 100% I | 4.5 | 0.5 |
| | 8 | 100% C | 4.5 | 0.5 |
| | 9 | 80% E / 20% F | 9.1 | 1.0 |
| Film 10 | 1 | 65% A / 35% B | 27.3 | 3.0 |
| | 2 | 100% C | 4.5 | 0.5 |
| | 3 | 100% I | 4.5 | 0.5 |
| | 4 | 100% C | 4.5 | 0.5 |
| | 5 | 100% M | 36.4 | 4.0 |
| | 6 | 100% C | 4.5 | 0.5 |
| | 7 | 100% I | 4.5 | 0.5 |
| | 8 | 100% C | 4.5 | 0.5 |
| | 9 | 80% E / 20% F | 9.1 | 1.0 |
| Film 11 | 1 | 65% A / 35% B | 27.3 | 3.0 |
| | 2 | 100% C | 4.5 | 0.5 |
| | 3 | 100% I | 4.5 | 0.5 |
| | 4 | 100% C | 4.5 | 0.5 |
| | 5 | 100% N | 36.4 | 4.0 |
| | 6 | 100% C | 4.5 | 0.5 |
| | 7 | 100% I | 4.5 | 0.5 |
| | 8 | 100% C | 4.5 | 0.5 |
| | 9 | 80% E / 20% F | 9.1 | 1.0 |
| Film 12 | 1 | 65% A / 35% B | 27.3 | 3.0 |
| | 2 | 100% C | 4.5 | 0.5 |
| | 3 | 100% I | 4.5 | 0.5 |
| | 4 | 100% C | 4.5 | 0.5 |
| | 5 | 100% O | 36.4 | 4.0 |
| | 6 | 100% C | 4.5 | 0.5 |
| | 7 | 100% I | 4.5 | 0.5 |
| | 8 | 100% C | 4.5 | 0.5 |
| | 9 | 80% E / 20% F | 9.1 | 1.0 |
| Film 13 | 1 | 80% B / 20% A | 30 | 3.0 |
| | 2 | 80% P / 20% Q | 5.0 | 0.5 |
| | 3 | 100% I | 5.0 | 0.5 |
| | 4 | 80% P / 20% Q | 5.0 | 0.5 |
| | 5 | 100% B | 35.0 | 3.5 |
| | 6 | 80% P / 20% Q | 5.0 | 0.5 |
| | 7 | 100% I | 5.0 | 0.5 |
| | 8 | 100% R | 5.0 | 0.5 |
| | 9 | 95% S / 5% T | 5.0 | 0.5 |
| Film 14 | 1 | 80% B / 20% A | 30 | 3.0 |
| | 2 | 80% P / 20% Q | 5.0 | 0.5 |
| | 3 | 100% J | 5.0 | 0.5 |
| | 4 | 80% P / 20% Q | 5.0 | 0.5 |
| | 5 | 100% B | 35.0 | 3.5 |
| | 6 | 80% P / 20% Q | 5.0 | 0.5 |
| | 7 | 100% J | 5.0 | 0.5 |
| | 8 | 100% R | 5.0 | 0.5 |
| | 9 | 95% S / 5% T | 5.0 | 0.5 |
| Film 15 | 1 | 80% B / 20% A | 30 | 3.0 |
| | 2 | 80% P / 20% Q | 5.0 | 0.5 |
| | 3 | 80% J / 20% H | 5.0 | 0.5 |
| | 4 | 80% P / 20% Q | 5.0 | 0.5 |
| | 5 | 100% B | 35.0 | 3.5 |
| | 6 | 80% P / 20% Q | 5.0 | 0.5 |
| | 7 | 80% J / 20% H | 5.0 | 0.5 |
| | 8 | 100% R | 5.0 | 0.5 |
| | 9 | 95% S / 5% T | 5.0 | 0.5 |
| Film 16 | 1 | 80% B / 20% A | 30 | 3.0 |
| | 2 | 80% P / 20% Q | 5.0 | 0.5 |
| | 3 | 80% J / 20% H | 5.0 | 0.5 |
| | 4 | 80% P / 20% Q | 5.0 | 0.5 |
| | 5 | 100% B | 35.0 | 3.5 |
| | 6 | 80% P / 20% Q | 5.0 | 0.5 |
| | 7 | 80% J / 20% H | 5.0 | 0.5 |
| | 8 | 100% R | 5.0 | 0.5 |
| | 9 | 85% S / 15% U | 5.0 | 0.5 |
| Film 17 | 1 | 80% B / 20% A | 30.0 | 3.0 |
| | 2 | 100% R | 5.0 | 0.5 |
| | 3 | 100% D | 3.0 | 0.3 |
| | 4 | 100% R | 5.0 | 0.5 |
| | 5 | 100% B | 35.0 | 3.9 |
| | 6 | 100% R | 5.0 | 0.5 |
| | 7 | 100% D | 3.0 | 0.3 |
| | 8 | 100% R | 5.0 | 0.5 |
| | 9 | 99.05% S / 0.5% W / 0.45% T | 5.0 | 0.5 |
| Film 18 | 1 | 80% B / 20% A | 30.0 | 3.0 |
| | 2 | 100% R | 5.0 | 0.5 |
| | 3 | 100% D | 3.0 | 0.3 |
| | 4 | 100% R | 5.0 | 0.5 |
| | 5 | 100% B | 35.0 | 3.9 |
| | 6 | 100% R | 5.0 | 0.5 |
| | 7 | 100% D | 3.0 | 0.3 |
| | 8 | 100% R | 5.0 | 0.5 |
| | 9 | 99.05% S / 0.5% W / 0.45% T | 5.0 | 0.5 |
| Film 19 | 1 | 80% B / 20% A | 30.0 | 3.0 |
| | 2 | 100% R | 5.0 | 0.5 |
| | 3 | 100% D | 3.0 | 0.3 |
| | 4 | 100% R | 5.0 | 0.5 |
| | 5 | 100% B | 35.0 | 3.9 |
| | 6 | 100% R | 5.0 | 0.5 |
| | 7 | 100% D | 3.0 | 0.3 |
| | 8 | 100% R | 5.0 | 0.5 |

TABLE 2-continued

| Film ID | Layer | Formulation | Volume % | Mils |
|---|---|---|---|---|
| | 9 | 99.05% S / 0.5% W / 0.45% T | 5.0 | 0.5 |
| Film 20 | 1 | 80% B / 20% A | 30.0 | 3.0 |
| | 2 | 100% R | 5.0 | 0.5 |
| | 3 | 100% D | 3.0 | 0.3 |
| | 4 | 100% R | 5.0 | 0.5 |
| | 5 | 100% B | 35.0 | 3.9 |
| | 6 | 100% R | 5.0 | 0.5 |
| | 7 | 100% D | 3.0 | 0.3 |
| | 8 | 100% R | 5.0 | 0.5 |
| | 9 | 99.05% S / 0.5% W / 0.45% T | 5.0 | 0.5 |
| Film 21 | 1 | 80% B / 20% A | 30.0 | 3.0 |
| | 2 | 100% R | 5.0 | 0.5 |
| | 3 | 100% D | 3.0 | 0.3 |
| | 4 | 100% R | 5.0 | 0.5 |
| | 5 | 100% B | 35.0 | 3.9 |
| | 6 | 100% R | 5.0 | 0.5 |
| | 7 | 100% B | 3.0 | 0.3 |
| | 8 | 100% R | 5.0 | 0.5 |
| | 9 | 99.05% S / 0.5% W / 0.45% T | 5.0 | 0.5 |
| Film 22 | 1 | 80% B / 20% A | 30.0 | 3.0 |
| | 2 | 100% R | 5.0 | 0.5 |
| | 3 | 100% D | 3.0 | 0.3 |
| | 4 | 100% R | 5.0 | 0.5 |
| | 5 | 100% B | 35.0 | 3.9 |
| | 6 | 100% R | 5.0 | 0.5 |
| | 7 | 100% B | 3.0 | 0.3 |
| | 8 | 100% R | 5.0 | 0.5 |
| | 9 | 99.05% S / 0.5% W / 0.45% T | 5.0 | 0.5 |
| Film 23 | 1 | 80% B / 20% A | 30.0 | 3.0 |
| | 2 | 100% R | 5.0 | 0.5 |
| | 3 | 80% D / 20% V | 3.0 | 0.3 |
| | 4 | 100% R | 5.0 | 0.5 |
| | 5 | 100% B | 35.0 | 3.9 |
| | 6 | 100% R | 5.0 | 0.5 |
| | 7 | 100% B | 3.0 | 0.3 |
| | 8 | 100% R | 5.0 | 0.5 |
| | 9 | 99.05% S / 0.5% W / 0.45% T | 5.0 | 0.5 |
| Film 24 | 1 | 80% B / 20% A | 30.0 | 3.0 |
| | 2 | 100% R | 5.0 | 0.5 |
| | 3 | 80% D / 20% V | 3.0 | 0.3 |
| | 4 | 100% R | 5.0 | 0.5 |
| | 5 | 100% B | 35.0 | 3.9 |
| | 6 | 100% R | 5.0 | 0.5 |
| | 7 | 100% B | 3.0 | 0.3 |
| | 8 | 100% R | 5.0 | 0.5 |
| | 9 | 99.05% S / 0.5% W / 0.45% T | 5.0 | 0.5 |
| Film 25 | 1 | 80% B / 20% A | 30 | 3.0 |
| | 2 | 80% P / 20% Q | 5.0 | 0.5 |
| | 3 | 80% J / 20% H | 5.0 | 0.5 |
| | 4 | 80% P / 20% Q | 5.0 | 0.5 |
| | 5 | 100% B | 35.0 | 3.5 |
| | 6 | 80% P / 20% Q | 5.0 | 0.5 |
| | 7 | 80% J / 20% H | 5.0 | 0.5 |
| | 8 | 100% R | 5.0 | 0.5 |
| | 9 | 80% E / 20% F | 5.0 | 0.5 |
| Film 26 | 1 | 80% B / 20% A | 36.0 | 4.5 |
| | 2 | 100% R | 4.0 | 0.5 |
| | 3 | 100% D | 4.0 | 0.5 |
| | 4 | 100% R | 4.0 | 0.5 |
| | 5 | 100% B | 36.0 | 4.5 |
| | 6 | 100% R | 4.0 | 0.5 |
| | 7 | 80% J / 20% H | 4.0 | 0.5 |
| | 8 | 100% R | 4.0 | 0.5 |
| | 9 | 95% S / 5% Y | 4.0 | 0.5 |
| Film 27 | 1 | 80% B / 20% A | 36.0 | 4.5 |
| | 2 | 100% R | 4.0 | 0.5 |
| | 3 | 100% D | 4.0 | 0.5 |
| | 4 | 100% R | 4.0 | 0.5 |
| | 5 | 100% B | 36.0 | 4.5 |
| | 6 | 100% R | 4.0 | 0.5 |
| | 7 | 80% J / 20% H | 4.0 | 0.5 |
| | 8 | 100% R | 4.0 | 0.5 |
| | 9 | 99.05% S / 0.5% W / 0.45% T | 4.0 | 0.5 |
| Film 28 | 1 | 80% B / 20% A | 36.0 | 4.5 |
| | 2 | 100% Z | 4.0 | 0.5 |
| | 3 | 100% D | 4.0 | 0.5 |
| | 4 | 100% Z | 4.0 | 0.5 |
| | 5 | 100% B | 36.0 | 4.5 |
| | 6 | 100% Z | 4.0 | 0.5 |
| | 7 | 80% J / 20% H | 4.0 | 0.5 |
| | 8 | 100% Z | 4.0 | 0.5 |
| | 9 | 99.05% S / 0.5% W / 0.45% T | 4.0 | 0.5 |
| Film 29 | 1 | 80% B / 20% A | 36.0 | 4.5 |
| | 2 | 100% AA | 4.0 | 0.5 |
| | 3 | 100% D | 4.0 | 0.5 |
| | 4 | 100% AA | 4.0 | 0.5 |
| | 5 | 100% B | 36.0 | 4.5 |
| | 6 | 100% AA | 4.0 | 0.5 |
| | 7 | 80% J / 20% H | 4.0 | 0.5 |
| | 8 | 100% AA | 4.0 | 0.5 |
| | 9 | 99.05% S / 0.5% W / 0.45% T | 4.0 | 0.5 |
| Film 30 | 1 | 80% X / 20% A | 36.0 | 4.5 |
| | 2 | 100% R | 4.0 | 0.5 |
| | 3 | 100% D | 4.0 | 0.5 |
| | 4 | 100% R | 4.0 | 0.5 |
| | 5 | 100% X | 36.0 | 4.5 |
| | 6 | 100% R | 4.0 | 0.5 |
| | 7 | 80% J / 20% H | 4.0 | 0.5 |
| | 8 | 100% R | 4.0 | 0.5 |
| | 9 | 99.05% S / 0.5% W / 0.45% T | 4.0 | 0.5 |
| Film 31 | 1 | 80% BB / 20% A | 36.0 | 4.5 |
| | 2 | 100% R | 4.0 | 0.5 |
| | 3 | 100% D | 4.0 | 0.5 |
| | 4 | 100% R | 4.0 | 0.5 |
| | 5 | 100% BB | 36.0 | 4.5 |
| | 6 | 100% R | 4.0 | 0.5 |

TABLE 2-continued

| Film ID | Layer | Formulation | Volume % | Mils |
|---|---|---|---|---|
| | 7 | 80% J<br>20% H | 4.0 | 0.5 |
| | 8 | 100% R | 4.0 | 0.5 |
| | 9 | 99.05% S<br>0.5% W<br>0.45% T | 4.0 | 0.5 |
| Film 32 | 1 | 80% B<br>20% A | 36.0 | 4.5 |
| | 2 | 100% P | 4.0 | 0.5 |
| | 3 | 100% CC | 4.0 | 0.5 |
| | 4 | 100% P | 4.0 | 0.5 |
| | 5 | 100% B | 36.0 | 4.5 |
| | 6 | 100% P | 4.0 | 0.5 |
| | 7 | 80% J<br>20% H | 4.0 | 0.5 |
| | 8 | 100% R | 4.0 | 0.5 |
| | 9 | 99.05% S<br>0.5% W<br>0.45% T | 4.0 | 0.5 |
| Film 33 | 1 | 80% B<br>20% A | 36.0 | 4.5 |
| | 2 | 100% R | 4.0 | 0.5 |
| | 3 | 100% D | 4.0 | 0.5 |
| | 4 | 100% R | 4.0 | 0.5 |
| | 5 | 100% B | 36.0 | 4.5 |
| | 6 | 100% R | 4.0 | 0.5 |
| | 7 | 100% CC | 4.0 | 0.5 |
| | 8 | 100% R | 4.0 | 0.5 |
| | 9 | 99.05% S<br>0.5% W<br>0.45% T | 4.0 | 0.5 |
| Film 34 | 1 | 80% B<br>20% A | 36.0 | 4.5 |
| | 2 | 100% R | 4.0 | 0.5 |
| | 3 | 100% B | 4.0 | 0.5 |
| | 4 | 100% R | 4.0 | 0.5 |
| | 5 | 100% B | 36.0 | 4.5 |
| | 6 | 100% R | 4.0 | 0.5 |
| | 7 | 100% B | 4.0 | 0.5 |
| | 8 | 100% R | 4.0 | 0.5 |
| | 9 | 99.05% S<br>0.5% W<br>0.45% T | 4.0 | 0.5 |
| Film 35 | 1 | 80% BB<br>20% A | 36.0 | 4.5 |
| | 2 | 100% R | 4.0 | 0.5 |
| | 3 | 100% D | 4.0 | 0.5 |
| | 4 | 100% R | 4.0 | 0.5 |
| | 5 | 100% BB | 36.0 | 4.5 |
| | 6 | 100% R | 4.0 | 0.5 |
| | 7 | 100% BB | 4.0 | 0.5 |
| | 8 | 100% R | 4.0 | 0.5 |
| | 9 | 99.05% S<br>0.5% W<br>0.45% T | 4.0 | 0.5 |
| Film 36 | 1 | 80% BB<br>20% A | 36.0 | 4.5 |
| | 2 | 100% R | 4.0 | 0.5 |
| | 3 | 100% D | 4.0 | 0.5 |
| | 4 | 100% R | 4.0 | 0.5 |
| | 5 | 100% BB | 36.0 | 4.5 |
| | 6 | 100% R | 4.0 | 0.5 |
| | 7 | 100% CC | 4.0 | 0.5 |
| | 8 | 100% R | 4.0 | 0.5 |
| | 9 | 99.05% S<br>0.5% W<br>0.45% T | 4.0 | 0.5 |
| Film 37 | 1 | 80% BB<br>20% A | 36.0 | 4.5 |
| | 2 | 100% P | 4.0 | 0.5 |
| | 3 | 70% CC<br>30% D | 4.0 | 0.5 |
| | 4 | 100% P | 4.0 | 0.5 |
| | 5 | 100% BB | 36.0 | 4.5 |
| | 6 | 100% P | 4.0 | 0.5 |
| | 7 | 80% FF<br>20% H | 4.0 | 0.5 |
| | 8 | 100% R | 4.0 | 0.5 |
| | 9 | 95% S<br>5% Y | 4.0 | 0.5 |
| Film 38 | 1 | 80% GG<br>20% A | 23.1 | 3.0 |
| | 2 | 100% FF | 7.7 | 1.0 |
| | 3 | 100% GG | 3.8 | 0.5 |
| | 4 | 100% FF | 7.7 | 1.0 |
| | 5 | 100% GG | 30.8 | 4.0 |
| | 6 | 100% FF | 7.7 | 1.0 |
| | 7 | 100% GG | 3.8 | 0.5 |
| | 8 | 100% R | 7.7 | 1.0 |
| | 9 | 95% S<br>2% T | 7.7 | 1.0 |
| Film 39 | 1 | 80% GG<br>20% A | 23.1 | 3.0 |
| | 2 | 80% FF<br>20% GG | 7.7 | 1.0 |
| | 3 | 100% H | 3.8 | 0.5 |
| | 4 | 80% FF<br>20% GG | 7.7 | 1.0 |
| | 5 | 100% GG | 30.8 | 4.0 |
| | 6 | 80% FF<br>20% GG | 7.7 | 1.0 |
| | 7 | 100% H | 3.8 | 0.5 |
| | 8 | 100% R | 7.7 | 1.0 |
| | 9 | 95% S<br>2% T | 7.7 | 1.0 |
| Film 40 | 1 | 80% GG<br>20% A | 23.1 | 3.0 |
| | 2 | 80% FF<br>20% GG | 7.7 | 1.0 |
| | 3 | 100% CC | 3.8 | 0.5 |
| | 4 | 80% FF<br>20% GG | 7.7 | 1.0 |
| | 5 | 100% GG | 30.8 | 4.0 |
| | 6 | 80% FF<br>20% GG | 7.7 | 1.0 |
| | 7 | 80% EE<br>20% H | 3.8 | 0.5 |
| | 8 | 100% R | 7.7 | 1.0 |
| | 9 | 95% S<br>2% T | 7.7 | 1.0 |
| Film 41 | 1 | 80% GG<br>20% A | 23.1 | 3.0 |
| | 2 | 80% FF<br>20% GG | 7.7 | 1.0 |
| | 3 | 100% CC | 3.8 | 0.5 |
| | 4 | 80% FF<br>20% GG | 7.7 | 1.0 |
| | 5 | 100% JJ | 30.8 | 4.0 |
| | 6 | 80% FF<br>20% GG | 7.7 | 1.0 |
| | 7 | 80% EE<br>20% H | 3.8 | 0.5 |
| | 8 | 100% R | 7.7 | 1.0 |
| | 9 | 95% S<br>2% T | 7.7 | 1.0 |
| Film 42 | 1 | 80% GG<br>20% A | 23.1 | 3.0 |
| | 2 | 80% FF<br>20% GG | 7.7 | 1.0 |
| | 3 | 100% CC | 3.8 | 0.5 |
| | 4 | 80% FF<br>20% GG | 7.7 | 1.0 |
| | 5 | 100% HH | 30.8 | 4.0 |
| | 6 | 80% FF<br>20% GG | 7.7 | 1.0 |
| | 7 | 80% EE<br>20% H | 3.8 | 0.5 |
| | 8 | 100% R | 7.7 | 1.0 |
| | 9 | 95% S<br>2% T | 7.7 | 1.0 |
| Film 43 | 1 | 80% GG<br>20% A | 23.1 | 3.0 |

TABLE 2-continued

Film Identification

| Film ID | Layer | Formulation | Volume % | Mils |
|---|---|---|---|---|
| | 2 | 80% FF<br>20% GG | 7.7 | 1.0 |
| | 3 | 100% CC | 3.8 | 0.5 |
| | 4 | 80% FF<br>20% GG | 7.7 | 1.0 |
| | 5 | 70% HH<br>30% II | 30.8 | 4.0 |
| | 6 | 80% FF<br>20% GG | 7.7 | 1.0 |
| | 7 | 80% EE<br>20% H | 3.8 | 0.5 |
| | 8 | 100% R | 7.7 | 1.0 |
| | 9 | 95% S<br>2% T | 7.7 | 1.0 |
| Film 44 | 1 | 80% GG<br>20% A | 23.1 | 3.0 |
| | 2 | 80% FF<br>20% GG | 7.7 | 1.0 |
| | 3 | 100% CC | 3.8 | 0.5 |
| | 4 | 80% FF<br>20% GG | 7.7 | 1.0 |
| | 5 | 70% JJ<br>30% II | 30.8 | 4.0 |
| | 6 | 80% FF<br>20% GG | 7.7 | 1.0 |
| | 7 | 80% EE<br>20% H | 3.8 | 0.5 |
| | 8 | 100% R | 7.7 | 1.0 |
| | 9 | 95% S<br>2% T | 7.7 | 1.0 |
| Film 45 | 1 | 80% GG<br>20% A | 23.1 | 3.0 |
| | 2 | 80% FF<br>20% GG | 7.7 | 1.0 |
| | 3 | 100% CC | 3.8 | 0.5 |
| | 4 | 80% FF<br>20% GG | 7.7 | 1.0 |
| | 5 | 70% GG<br>30% II | 30.8 | 4.0 |
| | 6 | 80% FF<br>20% GG | 7.7 | 1.0 |
| | 7 | 80% EE<br>20% H | 3.8 | 0.5 |
| | 8 | 100% R | 7.7 | 1.0 |
| | 9 | 95% S<br>5% T | 7.7 | 1.0 |
| Film 46 | 1 | 80% GG<br>20% A | 23.1 | 3.0 |
| | 2 | 80% FF<br>20% GG | 7.7 | 1.0 |
| | 3 | 100% CC | 3.8 | 0.5 |
| | 4 | 80% FF<br>20% GG | 7.7 | 1.0 |
| | 5 | 70% GG<br>30% KK | 30.8 | 4.0 |
| | 6 | 80% FF<br>20% GG | 7.7 | 1.0 |
| | 7 | 80% EE<br>20% H | 3.8 | 0.5 |
| | 8 | 100% R | 7.7 | 1.0 |
| | 9 | 95% S<br>5% T | 7.7 | 1.0 |
| Film 47 | 1 | 80% GG<br>20% A | 23.1 | 3.0 |
| | 2 | 80% FF<br>20% GG | 7.7 | 1.0 |
| | 3 | 100% CC | 3.8 | 0.5 |
| | 4 | 80% FF<br>20% GG | 7.7 | 1.0 |
| | 5 | 70% GG<br>30% LL | 30.8 | 4.0 |
| | 6 | 80% FF<br>20% GG | 7.7 | 1.0 |
| | 7 | 80% EE<br>20% H | 3.8 | 0.5 |
| | 8 | 100% R | 7.7 | 1.0 |
| | 9 | 95% S<br>5% T | 7.7 | 1.0 |
| Film 48 | 1 | 97% GG<br>3% MM | 23.1 | 3.0 |
| | 2 | 80% FF<br>20% GG | 7.7 | 1.0 |
| | 3 | 100% CC | 3.8 | 0.5 |
| | 4 | 80% FF<br>20% GG | 7.7 | 1.0 |
| | 5 | 100% GG | 30.8 | 4.0 |
| | 6 | 80% FF<br>20% GG | 7.7 | 1.0 |
| | 7 | 80% EE<br>20% H | 3.8 | 0.5 |
| | 8 | 100% R | 7.7 | 1.0 |
| | 9 | 95% S<br>5% T | 7.7 | 1.0 |
| Film 49 | 1 | 80% GG<br>20% A | 23.1 | 3.0 |
| | 2 | 80% FF<br>20% GG | 7.7 | 1.0 |
| | 3 | 100% CC | 3.8 | 0.5 |
| | 4 | 80% FF<br>20% GG | 7.7 | 1.0 |
| | 5 | 100% GG | 23.1 | 3.0 |
| | 6 | 80% FF<br>20% GG | 7.7 | 1.0 |
| | 7 | 80% EE<br>20% H | 3.8 | 0.5 |
| | 8 | 100% R | 15.4 | 2.0 |
| | 9 | 95% S<br>5% T | 7.7 | 1.0 |
| Film 50 | 1 | 80% GG<br>20% A | 23.1 | 3.0 |
| | 2 | 80% FF<br>20% GG | 7.7 | 1.0 |
| | 3 | 100% CC | 3.8 | 0.5 |
| | 4 | 80% FF<br>20% GG | 7.7 | 1.0 |
| | 5 | 100% GG | 30.8 | 4.0 |
| | 6 | 80% FF<br>20% GG | 7.7 | 1.0 |
| | 7 | 80% EE<br>20% H | 3.8 | 0.5 |
| | 8 | 100% R | 7.7 | 1.0 |
| | 9 | 65% S<br>30% NN<br>5% T | 7.7 | 1.0 |
| Film 51 | 1 | 80% PP<br>20% A | 23.1 | 3.0 |
| | 2 | 80% OO<br>20% PP | 7.7 | 1.0 |
| | 3 | 100% H | 3.8 | 0.5 |
| | 4 | 80% OO<br>20% PP | 7.7 | 1.0 |
| | 5 | 100% PP | 30.8 | 4.0 |
| | 6 | 80% OO<br>20% PP | 7.7 | 1.0 |
| | 7 | 100% H | 3.8 | 0.5 |
| | 8 | 100% R | 7.7 | 1.0 |
| | 9 | 95% XX<br>5% T | 7.7 | 1.0 |
| Film 52 | 1 | 80% PP<br>20% A | 23.1 | 3.0 |
| | 2 | 80% OO<br>20% PP | 7.7 | 1.0 |
| | 3 | 100% H | 3.8 | 0.5 |
| | 4 | 80% OO<br>20% PP | 7.7 | 1.0 |
| | 5 | 100% PP | 30.8 | 4.0 |
| | 6 | 80% OO<br>20% PP | 7.7 | 1.0 |
| | 7 | 80% QQ<br>20% H | 3.8 | 0.5 |
| | 8 | 100% R | 7.7 | 1.0 |

TABLE 2-continued

Film Identification

| Film ID | Layer | Formulation | Volume % | Mils |
|---|---|---|---|---|
| | 9 | 95% XX 5% T | 7.7 | 1.0 |
| Film 53 | 1 | 80% PP 20% A | 23.1 | 3.0 |
| | 2 | 80% OO 20% PP | 7.7 | 1.0 |
| | 3 | 80% QQ 20% H | 3.8 | 0.5 |
| | 4 | 80% OO 20% PP | 7.7 | 1.0 |
| | 5 | 100% PP | 30.8 | 4.0 |
| | 6 | 80% OO 20% PP | 7.7 | 1.0 |
| | 7 | 80% QQ 20% H | 3.8 | 0.5 |
| | 8 | 100% R | 7.7 | 1.0 |
| | 9 | 95% XX 5% T | 7.7 | 1.0 |
| Film 54 | 1 | 80% PP 20% A | 23.1 | 3.0 |
| | 2 | 80% OO 20% PP | 7.7 | 1.0 |
| | 3 | 100% CC | 3.8 | 0.5 |
| | 4 | 80% OO 20% PP | 7.7 | 1.0 |
| | 5 | 100% PP | 30.8 | 4.0 |
| | 6 | 80% OO 20% PP | 7.7 | 1.0 |
| | 7 | 80% QQ 20% H | 3.8 | 0.5 |
| | 8 | 100% R | 7.7 | 1.0 |
| | 9 | 95% XX 5% T | 7.7 | 1.0 |
| Film 55 | 1 | 80% PP 20% A | 23.1 | 3.0 |
| | 2 | 100% RR | 7.7 | 1.0 |
| | 3 | 100% D | 3.8 | 0.5 |
| | 4 | 100% RR | 7.7 | 1.0 |
| | 5 | 100% PP | 30.8 | 4.0 |
| | 6 | 100% RR | 7.7 | 1.0 |
| | 7 | 80% QQ 20% H | 3.8 | 0.5 |
| | 8 | 100% R | 7.7 | 1.0 |
| | 9 | 95% XX 5% T | 7.7 | 1.0 |
| Film 56 | 1 | 80% PP 20% A | 23.1 | 3.0 |
| | 2 | 80% OO 20% HH | 7.7 | 1.0 |
| | 3 | 100% CC | 3.8 | 0.5 |
| | 4 | 80% OO 20% HH | 7.7 | 1.0 |
| | 5 | 100% HH | 30.8 | 4.0 |
| | 6 | 80% OO 20% HH | 7.7 | 1.0 |
| | 7 | 80% QQ 20% H | 3.8 | 0.5 |
| | 8 | 100% R | 7.7 | 1.0 |
| | 9 | 95% XX 5% T | 7.7 | 1.0 |
| Film 57 | 1 | 80% PP 20% A | 23.1 | 3.0 |
| | 2 | 80% OO 20% HH | 7.7 | 1.0 |
| | 3 | 80% QQ 20% H | 3.8 | 0.5 |
| | 4 | 80% OO 20% HH | 7.7 | 1.0 |
| | 5 | 100% HH | 30.8 | 4.0 |
| | 6 | 80% OO 20% HH | 7.7 | 1.0 |
| | 7 | 80% QQ 20% H | 3.8 | 0.5 |
| | 8 | 100% R | 7.7 | 1.0 |
| | 9 | 95% XX 5% T | 7.7 | 1.0 |
| Film 58 | 1 | 80% PP 20% A | 23.1 | 3.0 |
| | 2 | 80% OO 20% PP | 7.7 | 1.0 |
| | 3 | 80% QQ 20% H | 3.8 | 0.5 |
| | 4 | 80% OO 20% PP | 7.7 | 1.0 |
| | 5 | 100% PP | 30.8 | 4.0 |
| | 6 | 80% OO 20% PP | 7.7 | 1.0 |
| | 7 | 80% QQ 20% H | 3.8 | 0.5 |
| | 8 | 100% RR | 7.7 | 1.0 |
| | 9 | 95% XX 5% T | 7.7 | 1.0 |
| Film 59 | 1 | 80% PP 20% A | 23.1 | 3.0 |
| | 2 | 80% OO 20% PP | 7.7 | 1.0 |
| | 3 | 80% QQ 20% H | 3.8 | 0.5 |
| | 4 | 80% OO 20% PP | 7.7 | 1.0 |
| | 5 | 100% PP | 30.8 | 4.0 |
| | 6 | 80% OO 20% PP | 7.7 | 1.0 |
| | 7 | 80% QQ 20% H | 3.8 | 0.5 |
| | 8 | 80% OO 20% PP | 7.7 | 1.0 |
| | 9 | 85% TT 15% F | 7.7 | 1.0 |
| Film 60 | 1 | 80% PP 20% A | 23.1 | 3.0 |
| | 2 | 80% OO 20% PP | 7.7 | 1.0 |
| | 3 | 80% QQ 20% H | 3.8 | 0.5 |
| | 4 | 80% OO 20% PP | 7.7 | 1.0 |
| | 5 | 100% PP | 30.8 | 4.0 |
| | 6 | 80% OO 20% PP | 7.7 | 1.0 |
| | 7 | 80% QQ 20% H | 3.8 | 0.5 |
| | 8 | 80% OO 20% PP | 7.7 | 1.0 |
| | 9 | 85% UU 15% F | 7.7 | 1.0 |
| Film 61 | 1 | 80% PP 20% YY | 23.1 | 3.0 |
| | 2 | 80% OO 20% PP | 7.7 | 1.0 |
| | 3 | 100% CC | 3.8 | 0.5 |
| | 4 | 80% OO 20% PP | 7.7 | 1.0 |
| | 5 | 100% PP | 30.8 | 4.0 |
| | 6 | 80% OO 20% PP | 7.7 | 1.0 |
| | 7 | 80% QQ 20% PP | 3.8 | 0.5 |
| | 8 | 100% R | 7.7 | 1.0 |
| | 9 | 95% XX 5% T | 7.7 | 1.0 |
| Film 62 | 1 | 80% PP 20% A | 23.1 | 3.0 |
| | 2 | 90% RR 10% HH | 7.7 | 1.0 |
| | 3 | 100% D | 3.8 | 0.5 |
| | 4 | 90% RR 10% HH | 7.7 | 1.0 |
| | 5 | 100% PP | 30.8 | 4.0 |
| | 6 | 90% RR 10% HH | 7.7 | 1.0 |
| | 7 | 80% QQ | 3.8 | 0.5 |

TABLE 2-continued

| Film ID | Layer | Formulation | Volume % | Mils |
|---|---|---|---|---|
| | | 20% H | | |
| | 8 | 100% R | 7.7 | 1.0 |
| | 9 | 95% XX | 7.7 | 1.0 |
| | | 5% T | | |
| Film 63 | 1 | 80% B | 23.1 | 3.0 |
| | | 20% A | | |
| | 2 | 100% R | 7.7 | 1.0 |
| | 3 | 100% O | 3.8 | 0.5 |
| | 4 | 100% R | 7.7 | 1.0 |
| | 5 | 100% B | 30.8 | 4.0 |
| | 6 | 100% R | 7.7 | 1.0 |
| | 7 | 80% EE | 3.8 | 0.5 |
| | | 20% H | | |
| | 8 | 100% R | 7.7 | 1.0 |
| | 9 | 95% S | 7.7 | 1.0 |
| | | 5% T | | |
| Film 64 | 1 | 80% BB | 23.1 | 3.0 |
| | | 20% A | | |
| | 2 | 100% R | 7.7 | 1.0 |
| | 3 | 100% O | 3.8 | 0.5 |
| | 4 | 100% R | 7.7 | 1.0 |
| | 5 | 100% BB | 30.8 | 4.0 |
| | 6 | 10% R | 7.7 | 1.0 |
| | 7 | 80% EE | 3.8 | 0.5 |
| | | 20% H | | |
| | 8 | 100% R | 7.7 | 1.0 |
| | 9 | 95% S | 7.7 | 1.0 |
| | | 5% T | | |
| Film 65 | 1 | 80% BB | 23.1 | 3.0 |
| | | 20% A | | |
| | 2 | 100% P | 7.7 | 1.0 |
| | 3 | 80% CC | 3.8 | 0.5 |
| | | 20% O | | |
| | 4 | 100% P | 7.7 | 1.0 |
| | 5 | 100% BB | 30.8 | 4.0 |
| | 6 | 100% P | 7.7 | 1.0 |
| | 7 | 80% EE | 3.8 | 0.5 |
| | | 20% H | | |
| | 8 | 100% R | 7.7 | 1.0 |
| | 9 | 95% S | 7.7 | 1.0 |
| | | 5% T | | |
| Film 66 | 1 | 80% BB | 23.1 | 3.0 |
| | | 20% A | | |
| | 2 | 100% P | 7.7 | 1.0 |
| | 3 | 70% CC | 3.8 | 0.5 |
| | | 30% O | | |
| | 4 | 100% P | 7.7 | 1.0 |
| | 5 | 100% BB | 30.8 | 4.0 |
| | 6 | 100% P | 7.7 | 1.0 |
| | 7 | 80% EE | 3.8 | 0.5 |
| | | 20% H | | |
| | 8 | 100% R | 7.7 | 1.0 |
| | 9 | 95% S | 7.7 | 1.0 |
| | | 5% T | | |
| Film 67 | 1 | 80% BB | 23.1 | 3.0 |
| | | 20% A | | |
| | 2 | 100% P | 7.7 | 1.0 |
| | 3 | 70% CC | 3.8 | 0.5 |
| | | 30% O | | |
| | 4 | 100% P | 7.7 | 1.0 |
| | 5 | 100% BB | 30.8 | 4.0 |
| | 6 | 100% P | 7.7 | 1.0 |
| | 7 | 80% EE | 3.8 | 0.5 |
| | | 20% H | | |
| | 8 | 100% R | 7.7 | 1.0 |
| | 9 | 95% S | 7.7 | 1.0 |
| | | 5% WW | | |
| Film 68 | 1 | 80% GG | 36.0 | 4.5 |
| | | 20% A | | |
| | 2 | 50% P | 4.0 | 0.5 |
| | | 50% R | | |
| | 3 | 100% D | 4.0 | 0.5 |
| | 4 | 50% P | 4.0 | 0.5 |
| | | 50% R | | |
| | 5 | 100% GG | 36.0 | 4.5 |
| | 6 | 50% P | 4.0 | 0.5 |
| | | 50% R | | |
| | 7 | 80% EE | 4.0 | 0.5 |
| | | 20% H | | |
| | 8 | 100% R | 4.0 | 0.5 |
| | 9 | 99.05% S | 4.0 | 0.5 |
| | | 0.5% W | | |
| | | 0.45% T | | |
| Film 69 | 1 | 80% GG | 33.3 | 3.5 |
| | | 20% A | | |
| | 2 | 50% P | 4.8 | 0.5 |
| | | 50% R | | |
| | 3 | 100% D | 4.8 | 0.5 |
| | 4 | 50% P | 4.8 | 0.5 |
| | | 50% R | | |
| | 5 | 100% GG | 33.3 | 3.5 |
| | 6 | 50% P | 4.8 | 0.5 |
| | | 50% R | | |
| | 7 | 80% EE | 4.8 | 0.5 |
| | | 20% H | | |
| | 8 | 100% R | 4.8 | 0.5 |
| | 9 | 99.05% S | 4.8 | 0.5 |
| | | 0.5% W | | |
| | | 0.45% T | | |
| Film 70 | 1 | 80% GG | 29.4 | 2.5 |
| | | 20% A | | |
| | 2 | 50% P | 5.8 | 0.5 |
| | | 50% R | | |
| | 3 | 100% D | 5.8 | 0.5 |
| | 4 | 50% P | 5.8 | 0.5 |
| | | 50% R | | |
| | 5 | 100% GG | 29.4 | 2.5 |
| | 6 | 50% P | 5.8 | 0.5 |
| | | 50% R | | |
| | 7 | 80% EE | 5.8 | 0.5 |
| | | 20% H | | |
| | 8 | 100% R | 5.8 | 0.5 |
| | 9 | 99.05% S | 5.8 | 0.5 |
| | | 0.5% W | | |
| | | 0.45% T | | |
| Film 71 | 1 | 80% GG | 36.0 | 4.5 |
| | | 20% A | | |
| | 2 | 100% FF | 4.0 | 0.5 |
| | 3 | 100% CC | 4.0 | 0.5 |
| | 4 | 100% FF | 4.0 | 0.5 |
| | 5 | 100% GG | 36.0 | 4.5 |
| | 6 | 100% FF | 4.0 | 0.5 |
| | 7 | 80% EE | 4.0 | 0.5 |
| | 8 | 20% H | 4.0 | 0.5 |
| | 9 | 99.05% S | 4.0 | 0.5 |
| | | 0.5% W | | |
| | | 0.45% T | | |
| Film 72 | 1 | 80% GG | 33.3 | 3.5 |
| | | 20% A | | |
| | 2 | 100% FF | 4.8 | 0.5 |
| | 3 | 100% CC | 4.8 | 0.5 |
| | 4 | 100% FF | 4.8 | 0.5 |
| | 5 | 100% GG | 33.3 | 3.5 |
| | 6 | 100% FF | 4.8 | 0.5 |
| | 7 | 80% EE | 4.8 | 0.5 |
| | 8 | 20% H | 4.8 | 0.5 |
| | 9 | 99.05% S | 4.8 | 0.5 |
| | | 0.5% W | | |
| | | 0.45% T | | |
| Film 73 | 1 | 80% GG | 29.4 | 2.5 |
| | | 20% A | | |
| | 2 | 100% FF | 5.8 | 0.5 |
| | 3 | 100% CC | 5.8 | 0.5 |
| | 4 | 100% FF | 5.8 | 0.5 |
| | 5 | 100% GG | 29.4 | 2.5 |
| | 6 | 100% FF | 5.8 | 0.5 |
| | 7 | 80% EE | 5.8 | 0.5 |
| | 8 | 20% H | 5.8 | 0.5 |
| | 9 | 99.05% S | 5.8 | 0.5 |
| | | 0.5% W | | |
| | | 0.45% T | | |

TABLE 2-continued

| Film ID | Layer | Formulation | Volume % | Mils |
|---|---|---|---|---|
| Film 74 | 1 | 80% GG | 36.0 | 4.5 |
|  |  | 20% A |  |  |
|  | 2 | 100% FF | 4.0 | 0.5 |
|  | 3 | 80% EE | 4.0 | 0.5 |
|  |  | 20% H |  |  |
|  | 4 | 100% FF | 4.0 | 0.5 |
|  | 5 | 100% GG | 36.0 | 4.5 |
|  | 6 | 100% FF | 4.0 | 0.5 |
|  | 7 | 80% EE | 4.0 | 0.5 |
|  |  | 20% H |  |  |
|  | 8 | 100% R | 4.0 | 0.5 |
|  | 9 | 99.05% S | 4.0 | 0.5 |
|  |  | 0.5% W |  |  |
|  |  | 0.45% T |  |  |
| Film 75 | 1 | 80% GG | 33.3 | 3.5 |
|  |  | 20% A |  |  |
|  | 2 | 100% FF | 4.8 | 0.5 |
|  | 3 | 80% EE | 4.8 | 0.5 |
|  |  | 20% H |  |  |
|  | 4 | 100% EF | 4.8 | 0.5 |
|  | 5 | 100% GG | 33.3 | 3.5 |
|  | 6 | 100% FF | 4.8 | 0.5 |
|  | 7 | 80% EE | 4.8 | 0.5 |
|  |  | 20% H |  |  |
|  | 8 | 100% R | 4.8 | 0.5 |
|  | 9 | 99.05% S | 4.8 | 0.5 |
|  |  | 0.5% W |  |  |
|  |  | 0.45% T |  |  |
| Film 76 | 1 | 80% GG | 29.4 | 2.5 |
|  |  | 20% A |  |  |
|  | 2 | 100% FF | 5.8 | 0.5 |
|  | 3 | 80% EE | 5.8 | 0.5 |
|  |  | 20% H |  |  |
|  | 4 | 100% FF | 5.8 | 0.5 |
|  | 5 | 100% GG | 29.4 | 2.5 |
|  | 6 | 100% FF | 5.8 | 0.5 |
|  | 7 | 80% EE | 5.8 | 0.5 |
|  |  | 20% H |  |  |
|  | 8 | 100% R | 5.8 | 0.5 |
|  | 9 | 99.05% S | 5.8 | 0.5 |
|  |  | 0.5% W |  |  |
|  |  | 0.45% T |  |  |
| Film 77 | 1 | 80% PP | 23.1 | 3.0 |
|  |  | 20% A |  |  |
|  | 2 | 100% OO | 7.7 | 1.0 |
|  | 3 | 100% CC | 3.8 | 0.5 |
|  | 4 | 100% OO | 7.7 | 1.0 |
|  | 5 | 70% PP | 26.9 | 3.5 |
|  |  | 30% Q |  |  |
|  | 6 | 100% OO | 7.7 | 1.0 |
|  | 7 | 80% QQ | 3.8 | 0.5 |
|  |  | 20% H |  |  |
|  | 8 | 100% OO | 7.7 | 1.0 |
|  | 9 | 100% R | 7.7 | 1.0 |
|  | 10 | 95% XX | 3.8 | 0.5 |
|  |  | 5% T |  |  |
| Film 78 | 1 | 80% PP | 23.1 | 3.0 |
|  |  | 20% A |  |  |
|  | 2 | 100% OO | 7.7 | 1.0 |
|  | 3 | 100% CC | 3.8 | 0.5 |
|  | 4 | 100% OO | 7.7 | 1.0 |
|  | 5 | 70% HH | 26.9 | 3.5 |
|  |  | 30% Q |  |  |
|  | 6 | 100% OO | 7.7 | 1.0 |
|  | 7 | 80% QQ | 3.8 | 0.5 |
|  |  | 20% H |  |  |
|  | 8 | 100% OO | 7.7 | 1.0 |
|  | 9 | 100% AAA | 7.7 | 1.0 |
|  | 10 | 95% XX | 3.8 | 0.5 |
|  |  | 5% T |  |  |
| Film 79 | 1 | 80% PP | 23.1 | 3.0 |
|  |  | 20% A |  |  |
|  | 2 | 100% OO | 7.7 | 1.0 |
|  | 3 | 100% CC | 3.8 | 0.5 |
|  | 4 | 100% OO | 7.7 | 1.0 |
|  | 5 | 100% PP | 34.6 | 4.5 |
|  | 6 | 100% OO | 7.7 | 1.0 |
|  | 7 | 80% QQ | 3.8 | 0.5 |
|  |  | 20% H |  |  |
|  | 8 | 100% OO | 7.7 | 1.0 |
|  | 9 | 100% BBB | 3.8 | 0.5 |
| Film 80 | 1 | 80% PP | 23.1 | 3.0 |
|  |  | 20% A |  |  |
|  | 2 | 100% OO | 7.7 | 1.0 |
|  | 3 | 100% CC | 3.8 | 0.5 |
|  | 4 | 100% OO | 7.7 | 1.0 |
|  | 5 | 100% PP | 34.6 | 4.5 |
|  | 6 | 100% OO | 7.7 | 1.0 |
|  |  | 80% QQ |  |  |
|  | 7 | 20% H | 3.8 | 0.5 |
|  | 8 | 100% OO | 7.7 | 1.0 |
|  | 9 | 100% CCC | 3.8 | 0.5 |
| Film 81 | 1 | 80% PP | 23.1 | 3.0 |
|  |  | 20% A |  |  |
|  | 2 | 100% OO | 7.7 | 1.0 |
|  | 3 | 100% CC | 3.8 | 0.5 |
|  | 4 | 100% OO | 7.7 | 1.0 |
|  | 5 | 100% PP | 34.6 | 4.5 |
|  | 6 | 100% OO | 7.7 | 1.0 |
|  | 7 | 80% QQ | 3.8 | 0.5 |
|  |  | 20% H |  |  |
|  | 8 | 100% OO | 7.7 | 1.0 |
|  | 9 | 100% DDD | 3.8 | 0.5 |

Example 1

Preparation of Films 1-76

Films 1-76 were manufactured by cast coextrusion. This method is well known to those of ordinary skill in the art.

Example 2

Oxygen Transmission Rate of Films 15, 17, 21, and 22 at 73° F. and 50/100% RH Out/In Oxygen transmission rate (OTR) was measured for Films 15, 17, 21, and 22 at 73° F. and 50/100% (out/in) relative humidity (RH), in accordance with ASTM D-3895. Results are shown in Table 3 below. FIG. 1 is a graph of the OTR of Films 15, 17, 21, and 22 over a course of 1-10 days. The data illustrates that EVOH by itself as a single or dual barrier is not sufficient for wet (100%/100% RH) conditions.

TABLE 3

OTR of Films 15, 17, 21, 22 at 50% RH Out, 100% RH In

| Days | OTR Film 15 (cc/m²-atm-day) | OTR Film 17 (cc/m²-atm-day) | OTR Film 21 (cc/m²-atm-day) | OTR Film 22 (cc/m²-atm-day) |
|---|---|---|---|---|
| 1 | 2.8 | 3.7 | 2.0 | 3.5 |
| 2 | 3.1 | 2.9 | 1.5 | 3.5 |
| 3 | 5.3 | 3.8 | 1.5 | 3.5 |
| 4 | 4.6 | 3.8 | 1.8 | 3.7 |
| 5 | 4.5 | 4.0 | 1.8 | 3.7 |
| 6 | 4.3 | 3.9 | 1.8 | 3.7 |
| 7 | 4.1 | 3.8 | 1.8 | 3.5 |
| 8 | 4.0 | 4.0 | 2.0 | 3.7 |
| 9 | 3.8 | 3.5 | 1.7 | 3.3 |
| 10 | 3.7 | 3.5 | 1.5 | 3.0 |

Example 3

Figure 2:
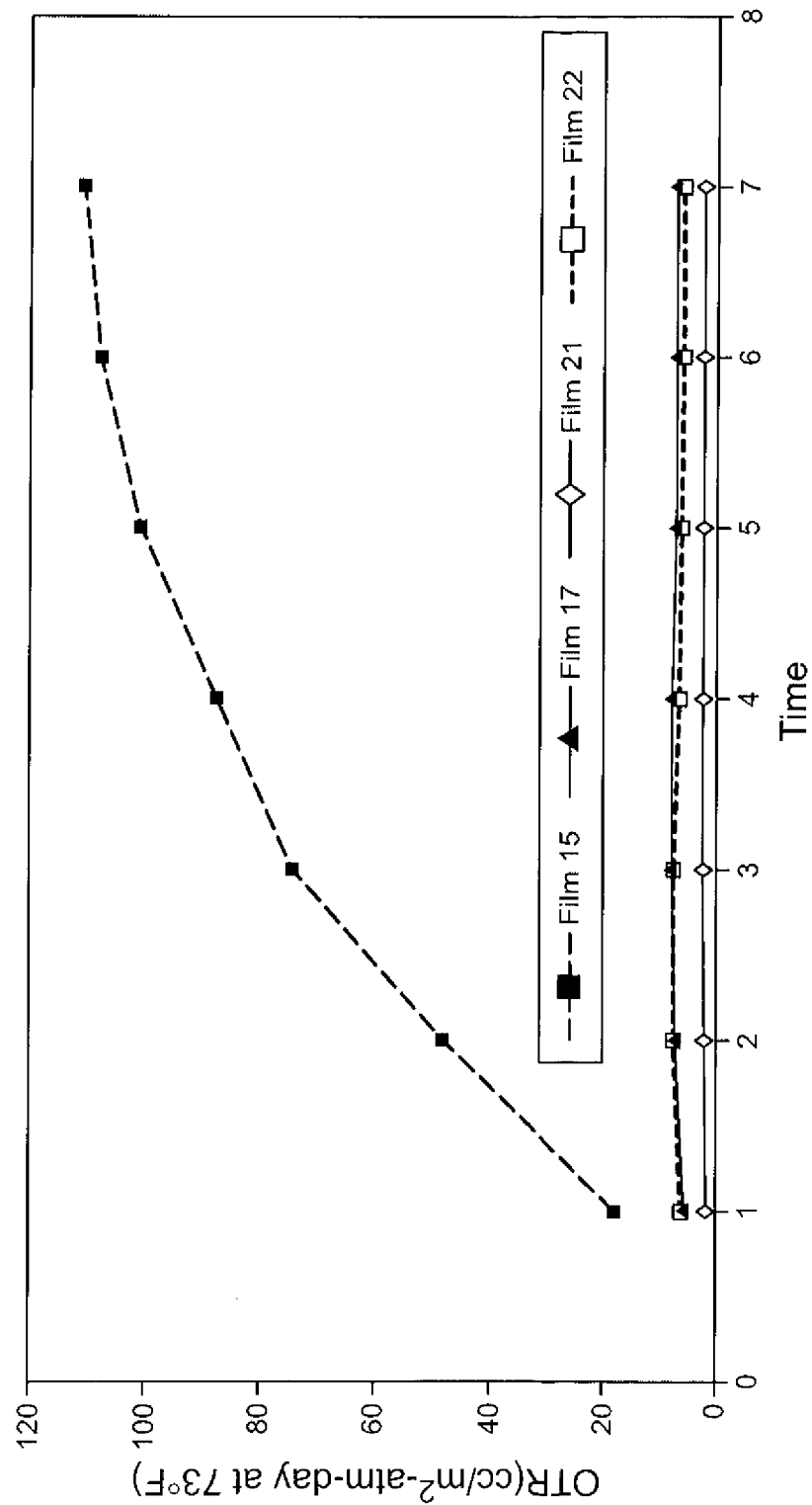
FIG. 2 is a line graph illustrating the oxygen transmission rate of disclosed Films 15, 17, 21, and 22 at 100/100% (in/out) relative humidity and 73° F. over a 7 day time course.

Oxygen Transmission Rate of Films 15, 17, 21, and 22 at 73° F. and 100/100% RH Out/In Oxygen transmission rate was measured for Films 15, 17, 21, and 22 at 73° F. and 100/100% (out/in) RH, in accordance with ASTM D-3895. Results are shown in Table 4 below. FIG. 2 is a graph of the OTR of Films 15, 17, 21, and 22 over a course of 1-7 days. The data shows that EVOH by itself as a single or dual barrier is not sufficient for wet (100%/100% RH) conditions.

TABLE 4

OTR of Films 15, 17, 21, and 22 at 100/100% RH Out/In

| Days | OTR Film 15 (cc/m²-atm-day) | OTR Film 17 (cc/m²-atm-day) | OTR Film 21 (cc/m²-atm-day) | OTR Film 22 (cc/m²-atm-day) |
|---|---|---|---|---|
| 1 | 18.1 | 6.1 | 6.0 | 1.8 |
| 2 | 48.9 | 7.8 | 7.5 | 2.2 |
| 3 | 74.8 | 8.1 | 7.4 | 2.5 |
| 4 | 87.7 | 8.0 | 6.9 | 2.4 |
| 5 | 101.0 | 7.6 | 6.5 | 2.2 |
| 6 | 108.0 | 7.3 | 6.5 | 2.3 |
| 7 | 111.0 | 7.3 | 6.4 | 2.3 |

Example 4

Figure 3:
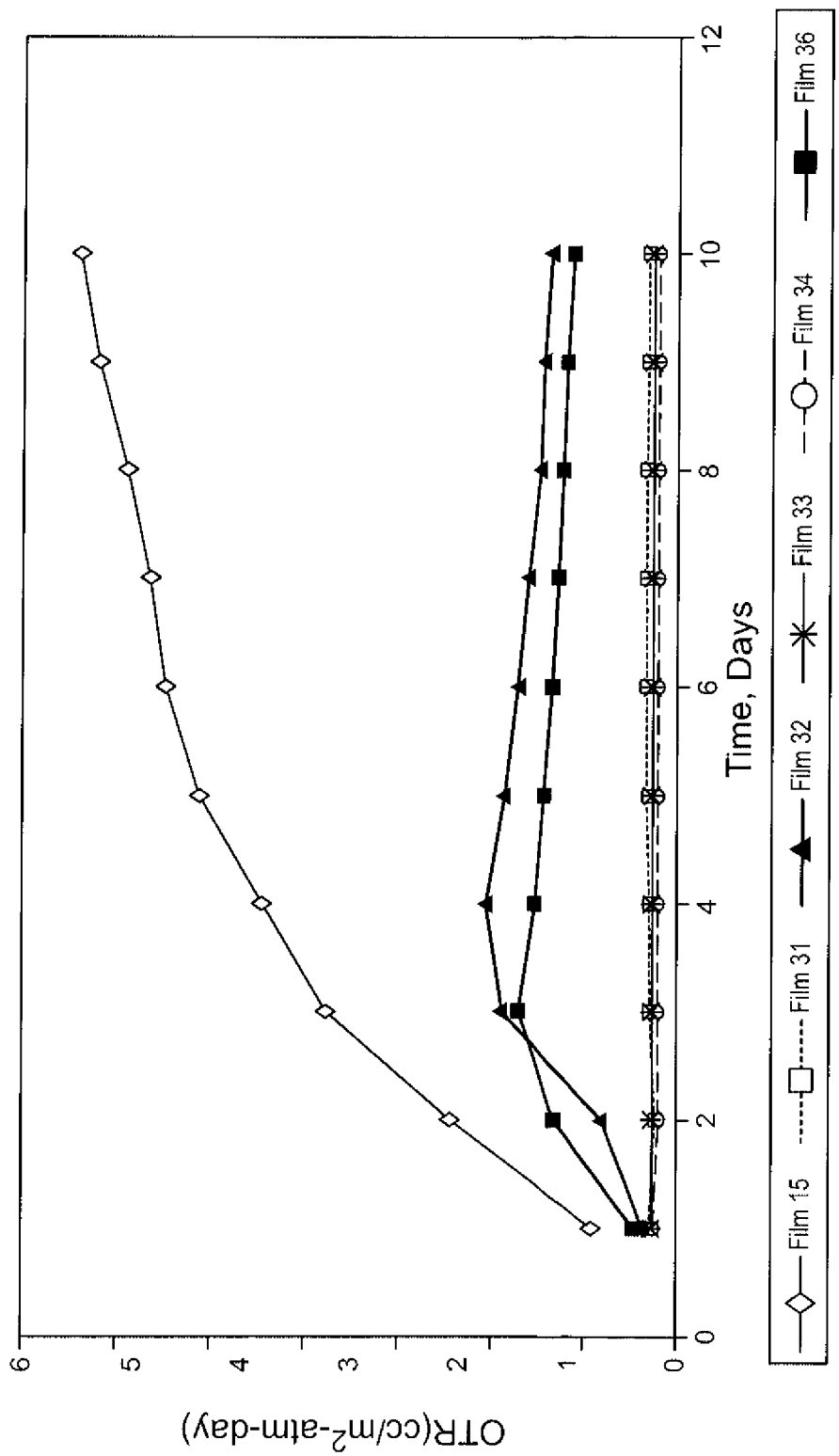
FIG. 3 is a line graph illustrating the oxygen transmission rate of disclosed Films 15, 31, 32, 33, 34, and 36 at 100/100% (in/out) relative humidity and 73° F. over a 10 day time course.

Oxygen Transmission Rate of Films 15, 31, 32, 33, 34, and 36 at 73° F. and 100/100% RH Out/In Oxygen transmission rate was measured for Films 15, 31, 32, 33, 34, and 36 at 73° F. and 100/100% (out/in) RH, in accordance with ASTM D-3895. Results are shown in Table 5 below. FIG. 3 is a graph of the OTR of Films 15, 31, 32, 33, 34, and 36 over a course of 1-10 days. The data again illustrates that EVOH by itself as a single or dual barrier is not sufficient for wet (100%/100% RH) conditions.

TABLE 5

OTR of Films 15, 31, 32, 33, 34, and 36 at 100/100% RH Out/In

| Days | Film 15 | Film 31 | Film 32 | Film 33 | Film 34 | Film 36 |
|---|---|---|---|---|---|---|
| 1 | 18.1 | 6.2 | 7.3 | 5.4 | 4.7 | 9.3 |
| 2 | 48.9 | 4.5 | 16.2 | 4.8 | 3.9 | 26.3 |
| 3 | 74.8 | 5.8 | 38.1 | 5.1 | 4.2 | 34.3 |
| 4 | 87.7 | 5.8 | 41.3 | 5.0 | 4.0 | 30.3 |
| 5 | 101.0 | 6.0 | 37.4 | 5.0 | 4.0 | 28.0 |
| 6 | 108.0 | 5.9 | 34.0 | 5.0 | 3.8 | 26.3 |
| 7 | 111.0 | 5.9 | 31.8 | 5.0 | 4.0 | 25.0 |
| 8 | 116.0 | 6.0 | 29.0 | 5.0 | 3.8 | 24.0 |
| 9 | 122.0 | 5.7 | 28.0 | 5.0 | 3.8 | 23.0 |
| 10 | 126.0 | 5.7 | 26.5 | 5.0 | 3.8 | 21.8 |

Example 5

Cell Density and Viability Testing

Film 67 was used to construct two rectangular bioprocessing containers (Bags 1 and 2) that hold a total volume of about 2 L and a working volume of about 1 L under standard aeration conditions. 2 standard commercial bioprocessing bags of the same size were used as a control. All 4 bags were sterilized with 25 KGy gamma radiation and were blown with sterile filtered air prior to cell inoculation.

Figure 4:
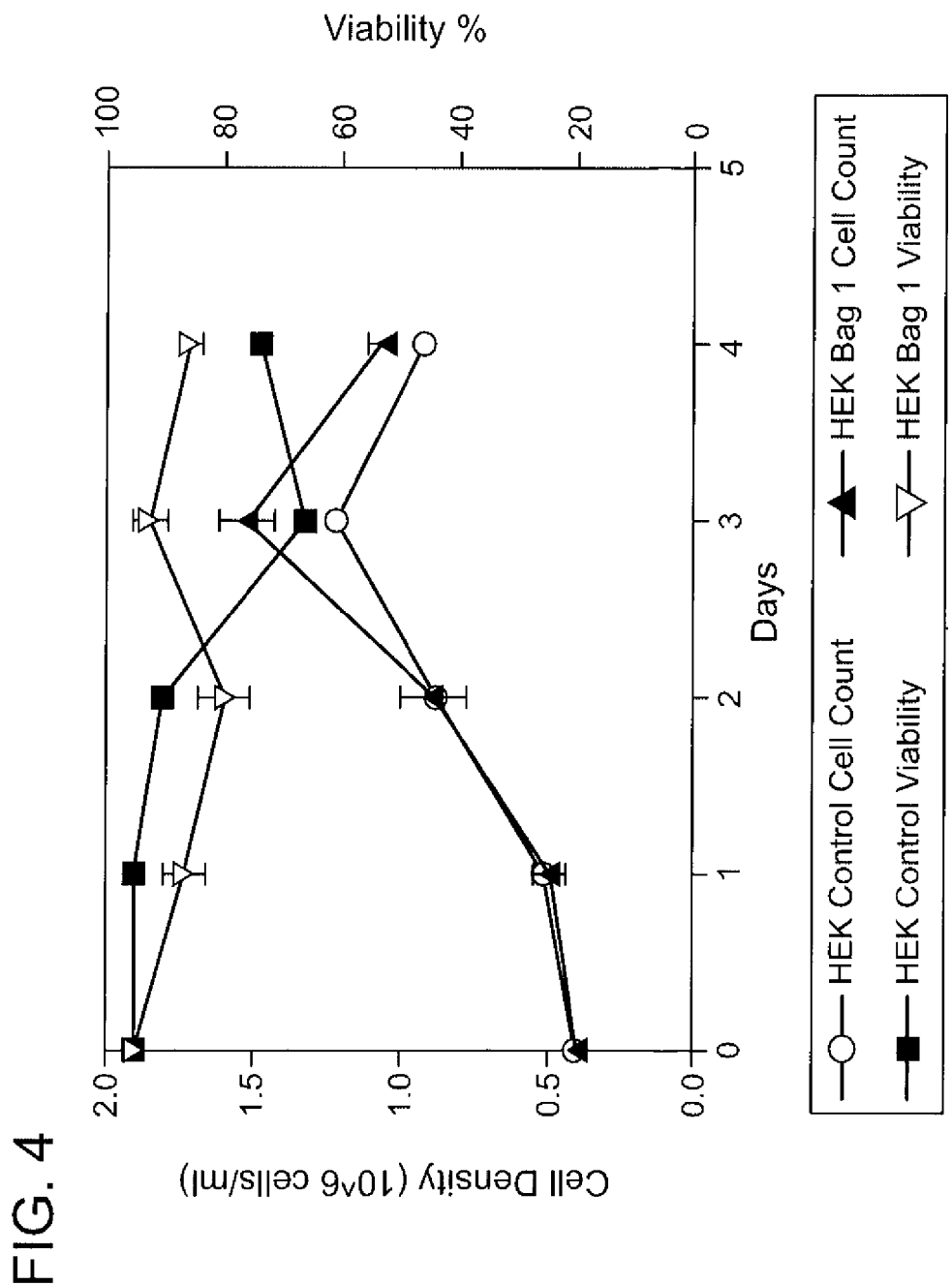
FIG. 4 is a line graph illustrating the human embryonic kidney (HEK) cell count and viability of a bioprocessing container constructed from disclosed Film 67 compared to a commercial bioprocessing container.
Figure 5:
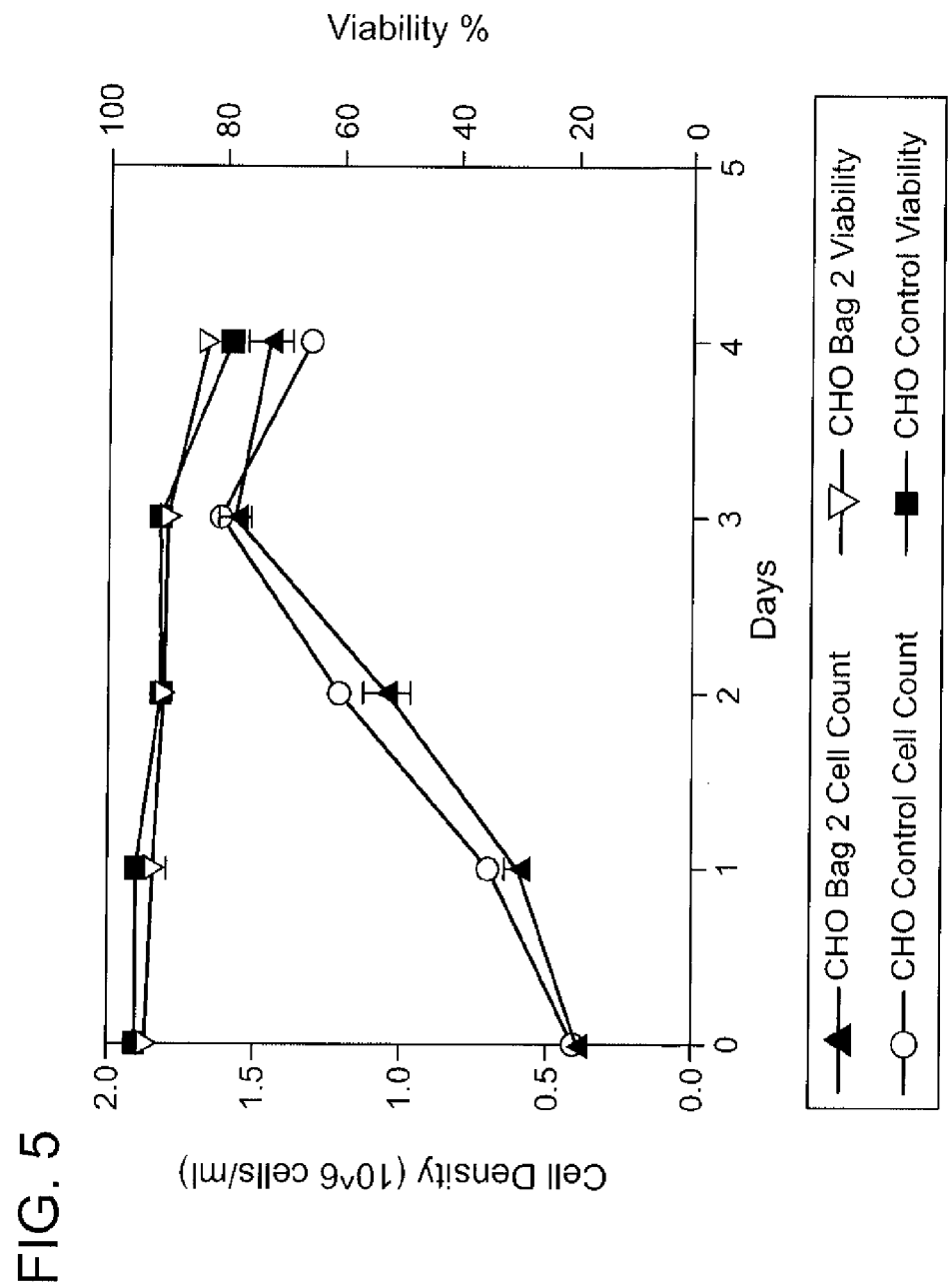
FIG. 5 is a line graph illustrating the Chinese hamster ovary (CHO) cell count and viability of a bioprocessing container constructed from disclosed Film 67 compared to a commercial bioprocessing container.

HEK cells (Human Embryonic Kidney 293 cells) were grown in shaking flasks and inoculated at $0.4 \times 10^6$ cells/mL in 300 mL of medium in Bag 1 and one control bag. CHO cells (Chinese hamster ovary cells) were grown in shaking flasks and inoculated at $0.4 \times 10^6$ cells/mL in 300 mL of medium in Bag 2 and one control bag. The bags were then placed in a bioreactor and incubated at 37° C. at 15 RPM rocking speed and an angle of 8 degrees. The cultures were monitored daily for cell density and viability. The data gathered through day 4 is given below in Tables 6 and 7 and are represented graphically in FIGS. 4 and 5. Data for Bags 1 and 2 was taken in duplicate.

From the data, it can be concluded that the performance of Bags 1 and 2 was comparable to the standard commercial bioprocessing bags. No significant differences were observed in term of cell density and viability between the bags for both the HEK and CHO cell lines.

TABLE 6

HEK Cell Viability and Density Testing

| | Day | | | | |
|---|---|---|---|---|---|
| ID | 0 | 1 | 2 | 3 | 4 |
| Bag 1 Cell Viability (%) | 95 | 83 | 75 | 95 | 83 |
| | 95 | 90 | 84 | 89 | 87 |
| Bag 1 Cell Count ($10^6$ cells/mL) | 0.41 | 0.44 | 0.77 | 1.42 | 1.1 |
| | 0.40 | 0.55 | 0.99 | 1.61 | 1.0 |
| Control Viability (%) | 95 | 95 | 90 | 66 | 73 |
| Control Cell Count ($10^6$ cells/mL) | 0.41 | 0.52 | 0.87 | 1.21 | 0.91 |

TABLE 7

CHO Cell Viability and Density Testing

| | Day | | | | |
|---|---|---|---|---|---|
| ID | 0 | 1 | 2 | 3 | 4 |
| Bag 2 Cell Viability (%) | 95 | 90 | 90 | 89 | 80 |
| | 95 | 94 | 91 | 90 | 85 |
| Bag 2 Cell Count ($10^6$ cells/mL) | 0.40 | 0.65 | 1.14 | 1.62 | 1.52 |
| | 0.40 | 0.54 | 0.97 | 1.51 | 1.37 |
| Control Viability (%) | 95 | 95 | 91 | 91 | 79 |
| Control Cell Count ($10^6$ cells/mL) | 0.40 | 0.70 | 1.21 | 1.61 | 1.31 |

Example 6

Oxygen Transmission Testing of Films 68-76

Oxygen transmission testing was conducted at 73° F. under 3 test conditions (0% RH, 50/100% RH in/out, and 100% RH) in accordance with ASTM D-3895 for Films 68-76. The data is given below in Table 8.

TABLE 8

OTR Testing of Films 68-76

| Film | OTR (cc/m²-atm-day) 0% RH | OTR (cc/m²-atm-day) 50% RH out/ 50% RH in | OTR (cc/m²-atm-day) 100% RH |
|---|---|---|---|
| 68 | 0.80 | 1.0 | 7.0 |
| 69 | 0.70 | 1.0 | 6.0 |
| 70 | 0.60 | 1.0 | 5.0 |

TABLE 8-continued

OTR Testing of Films 68-76

| Film | OTR (cc/m²-atm-day) 0% RH | OTR (cc/m²-atm-day) 50% RH out/ 50% RH in | OTR (cc/m²-atm-day) 100% RH |
|---|---|---|---|
| 71 | 0.80 | 1.0 | 23.0 |
| 72 | 0.70 | 1.0 | 25.0 |
| 73 | 0.80 | 1.0 | 24.0 |
| 74 | <0.20 | 1.0 | 50.0 |
| 75 | <0.20 | 1.0 | 53.0 |
| 76 | <0.20 | 1.0 | 79.0 |

Prophetic Example 7

Construction of Films 77-81

Films 77-81 will be constructed by cast coextrusion. This method is well known to those of ordinary skill in the art.

What is claimed is:

1. A multilayer film comprising:
   a. a sealant layer comprising:
      i. about 5-95 weight percent olefin hydrocarbon polymer with $T_g \geq 25°$ C.; and
      ii. about 95-5 weight percent alpha-olefin copolymer;
   b. a first barrier layer comprising polyglycolic acid, polyamide, EVOH, an EVOH blend, or combinations thereof, wherein the first barrier layer is positioned adjacent to the sealant layer;
   c. a skin layer comprising:
      i. PET; or
      ii. a PET blend, wherein at least one PET in the blend is amorphous and has $Tg \geq 50°$ C.; or
      iii. polyamide; or
      iv. a polyamide blend, wherein at least one polyamide in the blend is amorphous and has $Tg \geq 50°$ C.; and
   d. a second barrier layer comprising EVOH, an EVOH blend, or combinations thereof, wherein the second barrier layer is positioned adjacent to the skin layer;
wherein said film has an oxygen transmission rate of less than about 500 cc/m²-day-atm at 73° F. at high, intermediate, and low relative humidity conditions in accordance with ASTM D-3985.

2. The film of claim 1, wherein the olefin hydrocarbon polymer is selected from the group comprising: cyclic olefin copolymer, cyclic olefin homopolymer, poly(3-methyl-1-butene), poly(4-methyl-1 pentene), poly(3,3-dimethyl-1-butene), poly(4,4-dimethyl-1-pentene), poly(vinyl t-butyl ether), polystyrene, and combinations thereof.

3. The film of claim 1, wherein the alpha-olefin copolymer is selected from the group comprising: linear medium density polyethylene, linear low density polyethylene, and very low density polyethylene.

4. The film of claim 1, wherein the sealant layer comprises about 10-30 weight percent olefin hydrocarbon polymer and about 70-90 weight percent alpha olefin copolymer, based on the total weight of the sealant layer.

5. The film of claim 1, wherein the first barrier layer comprises a blend of about 1-50 weight percent polyglycolic acid and about 50-99 weight percent polyamide, based on the total weight of the layer.

6. The film of claim 1, wherein the first barrier layer comprises about 100% polyglycolic acid.

7. The film of claim 1, wherein the first barrier layer comprises about 100% polyamide, based on the total weight of the layer.

8. The film of claim 1, wherein the first barrier layer comprises about 100% EVOH or an EVOH blend, based on the total weight of the layer.

9. The film of claim 1, wherein the film is substantially free of film surface modifying additives.

10. The film of claim 1, wherein the EVOH or the EVOH blend of the second barrier layer comprises an ethylene content of between about 23 mol % and about 48 mol %.

11. A flexible bioprocessing container, said container comprising first and second flexible sidewalls constructed from the film of claim 1, wherein the sidewalls are sealed along their edges to define an interior compartment for housing a product.

12. The container of claim 11, wherein the container is a double walled container or a three-dimensional container.

13. The container of claim 11, wherein the container is pre-sterilized and disposable.

14. The container of claim 11, wherein the olefin hydrocarbon polymer of the film is selected from the group comprising: cyclic olefin copolymer, cyclic olefin homopolymer, poly(3-methyl-1-butene), poly(4-methyl-1-pentene), poly(3,3-dimethyl-1-butene), poly(4,4-dimethyl-1-pentene), poly(vinyl t-butyl ether), polystyrene, and combinations thereof.

15. The container of claim 11, wherein the EVOH or EVOH blend of the second barrier layer of the film comprises an ethylene content of between about 23 mol % and about 48 mol %.

16. A method of culturing cells, said method comprising:
   a. providing the flexible container of claim 11;
   b. introducing a liquid medium into the interior compartment of the container;
   c. inoculating the liquid medium with cells; and
   d. incubating the cells within the interior of the container under suitable conditions for cell growth.

17. The method of claim 16, wherein the container is pre-sterilized.

18. The method of claim 16, further comprising the step of agitating the container or container contents to thereby induce motion, whereby the necessary oxygen transfer and mixing required for cell growth and/or survival is accomplished by the motion of the agitation.

19. The method of claim 16, further comprising the step of introducing the flexible container to a heating system.

20. The method of claim 16, wherein the interior surface of the container has been treated by plasma discharge, corona discharge, gas plasma discharge, ion bombardment, ionizing radiation, high intensity UV light, or combinations thereof.

* * * * *